US011077126B2

(12) United States Patent
Jiang et al.

(10) Patent No.: US 11,077,126 B2
(45) Date of Patent: *Aug. 3, 2021

(54) USE OF CARRIMYCIN AND PHARMACEUTICALLY ACCEPTABLE SALTS OF CARRIMYCIN IN MANUFACTURING MEDICAMENT FOR TREATING AND/OR PREVENTING TUMOR

(71) Applicant: SHENYANG FUYANG PHARMACEUTICAL TECHNOLOGY CO., LTD., Liaoning (CN)

(72) Inventors: Enhong Jiang, Liaoning (CN); Mingyu Xia, Liaoning (CN); Xunlei Jiang, Liaoning (CN); Xundong Jiang, Liaoning (CN)

(73) Assignee: SHENYANG FUYANG PHARMACEUTICAL TECHNOLOGY CO., LTD., Liaoning (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/500,967

(22) PCT Filed: Apr. 5, 2018

(86) PCT No.: PCT/CN2018/082072
§ 371 (c)(1),
(2) Date: Oct. 4, 2019

(87) PCT Pub. No.: WO2018/184587
PCT Pub. Date: Oct. 11, 2018

(65) Prior Publication Data
US 2020/0030351 A1    Jan. 30, 2020

(30) Foreign Application Priority Data

Apr. 6, 2017  (CN) .......................... 201710221415.5

(51) Int. Cl.
*A61K 31/7048* (2006.01)
*A61P 35/02* (2006.01)
*A61K 45/06* (2006.01)

(52) U.S. Cl.
CPC .......... *A61K 31/7048* (2013.01); *A61P 35/02* (2018.01); *A61K 45/06* (2013.01)

(58) Field of Classification Search
CPC ................ C07H 17/08; A61K 31/7048; A61P 35/00–04
See application file for complete search history.

(56) References Cited

U.S. PATENT DOCUMENTS

| 5,602,106 | A * | 2/1997 | Ajito ................. C07H 17/08 514/30 |
| 7,795,001 | B2 | 9/2010 | Midoh et al. |
| 2011/0306571 | A1 | 12/2011 | Rosin-Arbesfeld |
| 2013/0150316 | A1 | 6/2013 | Jiang et al. |

FOREIGN PATENT DOCUMENTS

| CN | 1174238 A | 2/1998 |
| CN | 1405299 A | 3/2003 |
| CN | 1554355 A | 12/2004 |
| CN | 101649325 A | 2/2010 |
| CN | 102115757 A | 7/2011 |
| CN | 103142520 A | 6/2013 |
| CN | 103820474 A | 5/2014 |
| CN | 105497053 A | 4/2016 |
| CN | 105505954 A | 4/2016 |
| EP | 0 250 134 A1 | 12/1987 |
| JP | 2009-539970 A | 11/2009 |
| RU | 2 593 499 C2 | 8/2016 |
| WO | WO-2007144876 A1 * | 12/2007 ............. A61P 35/00 |

OTHER PUBLICATIONS

Wu, S. et al "Evaluating intrinsic and non-intrinsic cancer risk factors" Nature Comm., vol. 9, pp. 1-12. (Year: 2018).*
Derwent partial translation of CN 1405299. (Year: 2003).*
International Search Report (PCT/ISA/210) and translation and Written Opinion (PCT/ISA/237) dated Jul. 9, 2018, by the Chinese Patent Office as the International Searching Authority for International Application No. PCT/CN2018/082072.
Extended European Search Report dated Mar. 17, 2020, by the European Patent Office in corresponding European Patent Application No. 18781541.0. (8 pages).
Communication pursuant to Article 94(3) EPC dated Dec. 16, 2020, by the European Patent Office in corresponding European Patent Application No. 18781541.0. (5 pages).

(Continued)

*Primary Examiner* — Leigh C Maier
(74) *Attorney, Agent, or Firm* — Buchanan Ingersoll & Rooney PC

(57) ABSTRACT

The present disclosure provides use of carrimycin and pharmaceutically acceptable salts thereof for the preparation of a medicament for the treatment of tumors. The carrimycin and the pharmaceutically acceptable salts thereof have good curative effects on breast cancer, liver cancer, lung cancer, renal cancer, brain tumor, cervical cancer, prostate cancer, pancreatic cancer, esophageal cancer, gastric adenocarcinoma, colon cancer, lymphoma or leukemia and other tumors, and especially have obvious inhibitory effects on the growth of human breast cancer cells MCF-7 and MDA-MB-231, human hepatoma cells HepG2, human non-small cell lung cancer cells A549, human large cell lung cancer cells H460 and H1299, human renal clear cell adenocarcinoma cell 786-O, human renal cell adenocarcinoma cell 769-P, and human glioma cell U251.

14 Claims, 1 Drawing Sheet

(56) References Cited

OTHER PUBLICATIONS

Dembitsky, Valery M., "Astonishing Diversity of Natural Surfactants: 2. Polyether Glycosidic Ionophores and Macrocyclic Glycosides," Lipdids, 2005, vol. 40, No. 3, pp. 219-248.

Kawada et al., "Circumvention of Multidrug Resistance in Human Carcinoma KB Cells by Polyether Antibiotics," The Journal of Antibiotics, Apr. 1992, vol. 45, No. 4, pp. 556-562.

* cited by examiner

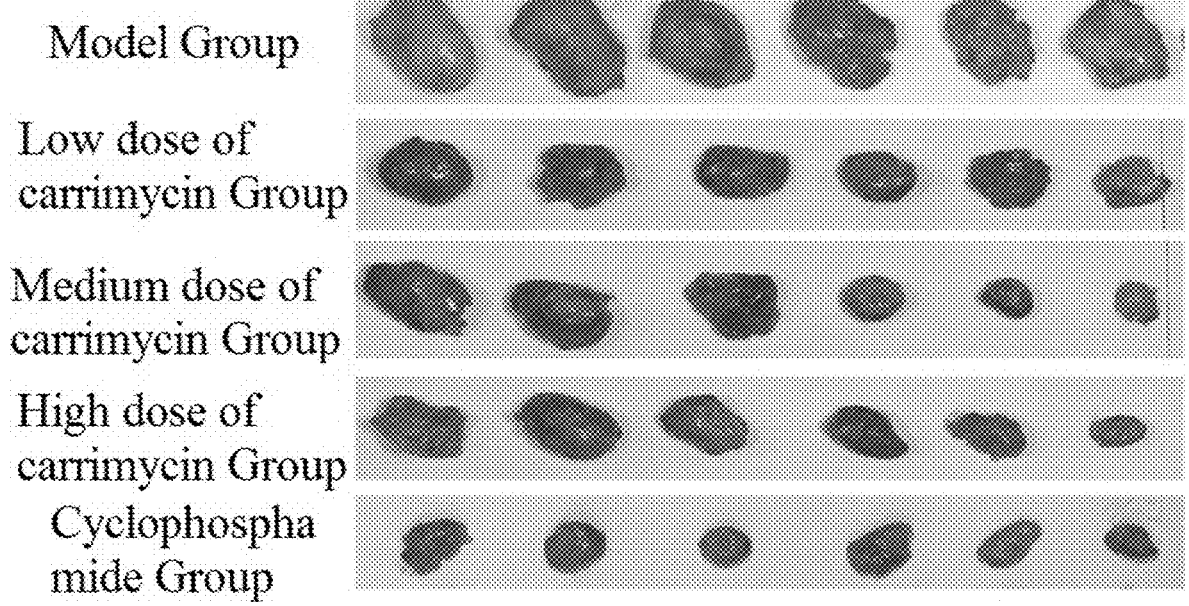

USE OF CARRIMYCIN AND PHARMACEUTICALLY ACCEPTABLE SALTS OF CARRIMYCIN IN MANUFACTURING MEDICAMENT FOR TREATING AND/OR PREVENTING TUMOR

TECHNICAL FIELD

The present disclosure belongs to the field of pharmaceutical application, and specifically relates to Use of carrimycin and pharmaceutically acceptable salts of carrimycin in manufacturing medicament for treating and/or preventing tumor.

BACKGROUND

Tumor is a common and frequently-occurring disease, and refers to the neoformation or neoplasm formed by clonal abnormal proliferation and differentiation caused by genetic mutation and loss of normal regulation of growth and differentiation of the histocyte of the organism under the long-term action of tumorigenic factors in vivo and in vitro. Tumors are classified into benign tumors and malignant tumors. The malignant tumors are further divided into three types: carcinomas derived from epithelial tissues, sarcomas derived from mesenchymal tissues, and carcinosarcomas. The term "cancer" is generally used to refer to all malignant tumors.

The malignant tumors are one of the major malignant diseases threatening human health and the first cause of death of the world's population. According to the latest statistics, in 2007, about 7.9 million people in the world died of various cancers, accounting for 13% of all deaths, and more than 12 million cancer cases were diagnosed, wherein 72% or more of tumor patients and deaths have occurred in underdeveloped countries, and it is rising continuously. In 2015, 9 million people in the world died of tumors, and it is expected that more than 12 million people will die of tumors in 2030. At present, the annual number of cancer cases in China is about 2.8 million, and the number of cancer deaths is more than 400,000, ranking first among all kinds of diseases in China, and showing a rising trend. With the speeding up of the pace of social life, the increasing pressure of competition, and the changes of human lifestyle and environment, tumor cases and deaths are rising year by year, and tumors have become the common diseases and the high incidence in modern society, not only seriously affecting the patients' life quality, but also bringing heavy economic and mental burden to the patients' families and the society. And tumors are also important social problems in the world, the treatment and prevention of cancer have always been one of the most pressing issues in the world. At present, chemotherapy is a main means of fighting against tumors. Although the chemotherapy has a better curative effect, the chemotherapy often causes side effects such as myelosuppression and low immune functions, making it difficult for patients to adhere to treatment. And drug resistance in the treatment process of chemotherapy has become one of the difficult problems in the current clinical treatment. In recent years, the global market of anti-tumor drugs has been growing rapidly. According to the statistics of the US FDA, the total sales of anti-cancer drugs in the world increased from 24 billion US dollars in 2004 to 39.6 billion US dollars in 2007. Although new anti-tumor drugs come out every year in the world, so far, there is still no effective means for humans to fight against cancer. At the same time, new types of cancer are constantly discovered, and the emergence and enhancement of tumor resistance/drug resistance make the need to find new effective anti-cancer drugs more and more urgent.

Carrimycin is a new type of antibiotic with the 4"-isovaleryl spiramycin as a main component, and carrimycin is formed by cloning the 4"-o-acyl-transferase of the carbomycin producing strain into a spiramycin producing strain by a transgenic technology, directionally acylating spiramycin 4"-OH, and adding an isovaleryl side chain at the 4"-position.

Carrimycin is composed of a variety of spiramycin derivatives with the main active component isovaleryl spiramycin (I+II+III) having a total content of no less than 60%, and is a pharmaceutically acceptable pharmaceutical composition. The central structure of the main component of the carrimycin is a 16-membered lactone ring, and the 16-membered lactone ring links one molecule of forosamine, one molecule of mycaminose and one molecule of mycarose. Its main component isovaleryl spiramycin I, II, III differs from the spiramycin structure in that the group connected to the 4'-position of mycarose is isovaleryl rather than hydroxyl. The drug is jointly declared by Tonglian Shengyang Group as the 1.1 type of new drug.

The chemical structure of the main component of carrimycin is shown as in a formula (I):

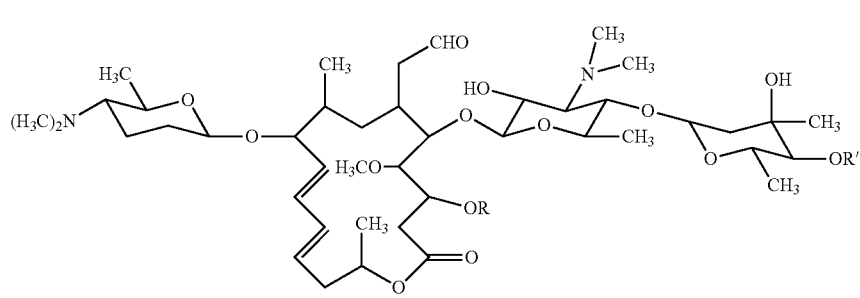

Formula (I)

Wherein, when R=H, R'=COCH$_2$CH(CH$_3$)$_2$, the main component is isovaleryl spiromycin I;

When R=COCH$_3$, R'=COCH$_2$CH(CH$_3$)$_2$, the main component is isovaleryl spiromycin II;

When R=COCH$_2$CH$_3$, R'=COCH$_2$CH(CH$_3$)$_2$, the main component is isovaleryl spiromycin III;

Carrimycin belongs to 16-membered macrolide antibiotics, has active groups such as a carboxyl group, an alkoxy group, an epoxy group, a ketone group and an aldehyde group, and a pair of conjugated C=C, and has a molecular weight of about 884 to 982. Carrimycin and macrolide antibiotics have many commonalities due to their similar chemical structures: they are easily soluble in most organic solvents such as esters, acetone, chloroform, alcohols, etc., slightly soluble in petroleum ether, and insoluble in water. Due to the presence of two dimethylamine groups in the molecular structure, carrimycin is alkalescence and easily soluble in an acidic aqueous solution. Carrimycin has a "negative solubility" property in which the solubility decreases with an increase temperature. Since isovaleryl spiramycin, the main component of carrimycin, has a longer carbon chain at the 4"-position and a poor hydrophilicity, the solubility of carrimycin in water is smaller than that of spiramycin and 4"-acetylspiramycin.

Carrimycin is white amorphous powder with slight hygroscopicity, and specific rotation of about −80.8°, maximum ultraviolet absorption wavelength of 231-232 nm. Carrimycin contains weak fluorescent chromophores, presents a purple reaction producing a strong purple fluorescence in case of concentrated sulfuric acid or hydrochloric acid, and has a maximum absorbance at 231-232 nm.

The drug has good lipophilicity, strong tissue penetration ability, rapid oral absorption, long body maintenance time, and sustained post antibiotic effects. According to a relationship between pharmacodynamics and chemical conformation, after the 4"-position of the macrolide antibiotics acylation, macrolide antibiotics have improved lipophilicity and in vivo activity, and significantly improved in vivo antibacterial activity and clinical therapeutic effects, and the in vivo stability of antibiotics enhances with the growing of the carbon chain of the 4"-hydroxy ester, that is, isovaleryl spiramycin>butyryl spiramycin>propionyl spiramycin>acetyl spiramycin.

The preliminary in vitro and in vivo pharmacodynamic tests showed that the drug not only has good antibacterial activity against most G$^+$ bacteria, but also has certain effects on some G$^−$ bacteria, and its technical indicators are obviously superior to those of azithromycin, erythromycin, acetyl spiramycin, and medemycin. It has the strongest antimicrobial activity especially against *Mycoplasma pneumoniae*, also has certain antimicrobial activity against the erythromycin resistant bacteria, gonococcus, pneumococcus, *Staphylococcus aureus, Bacillus pyocyaneus, Bacillus influenzae, Haemophilus influenzae, Bacteroides fragilis, legionella*, multi-line *bacillus* and *Clostridium perfringens*, and a tiny cross resistance against *Staphylococcus aureus* with clinical resistance to the erythromycin. Carrimycin will be primarily used to treat gram-positive infections, especially upper respiratory tract infections, and may be used for urinary tract infections.

In a recent study, the applicant found that through the evaluation of carrimycin against the in vitro antiproliferative activity of human breast cancer cells MCF-7 and MDA-MB-231, human hepatoma cells HepG2 or murine hepatoma cells H$_{22}$, human non-small cell lung cancer cells A549, Lewis lung cancer cells, human large cell lung cancer cells H460 and H1299, human renal clear cell adenocarcinoma cell 786-O, human renal cell adenocarcinoma cell 769-P, human glioma cell U251, human glioblastoma cell A172, human tissue lymphoma cell U937, human cervical cancer cell HeLa, human prostate cancer cell PC3, human pancreatic cancer cell PANC-1, human esophageal cancer cell TE-1, human gastric adenocarcinoma cell SGC7901, human colon cancer cell HT-29, and human promyelocytic leukemia cell HL-60, the samples showed good antiproliferative activity against the cells tested, indicating that carrimycin is expected to be a new drug for treating tumors, thereby completing the present disclosure.

SUMMARY

It is an object of the present disclosure to provide use of carrimycin and pharmaceutically acceptable salts thereof for the preparation of a medicament for the treatment and/or prevention of tumors.

To achieve the above object, the present disclosure adopts the following technical solution:

The present disclosure relates to the use of carrimycin and the pharmaceutically acceptable salts of carrimycin in manufacturing the medicament for treating and/or preventing tumor.

In the present disclosure, the tumor includes solid tumor and non-solid tumor.

Specifically, the solid tumor includes benign solid tumor and malignant solid tumor;

The non-solid tumors is lymphoma or leukemia.

Further, the malignant solid tumor is breast cancer, liver cancer, lung cancer, renal cancer, brain tumor, cervical cancer, prostate cancer, pancreatic cancer, esophageal cancer, gastric cancer, or colon cancer.

The brain tumor is glioma or meningioma, and the gastric cancer is gastric adenocarcinoma.

In the present disclosure, the medicament is in various formulations made of carrimycin and the pharmaceutically acceptable salts of carrimycin and pharmaceutically acceptable adjuvants.

In the present disclosure, the medicament is also in various formulations made of carrimycin and the pharmaceutically acceptable salts of carrimycin, and anti-tumor drugs and pharmaceutically acceptable adjuvants.

In the present disclosure, carrimycin and the pharmaceutically acceptable salts of carrimycin can be formulated into various compound preparations together with the anti-tumor drugs in the prior art such as oxaliplatin and the pharmaceutically acceptable adjuvants.

In the present disclosure, the medicament is further a combination of a first agent and a second agent, the first agent contains carrimycin and the pharmaceutically acceptable salts thereof, and the second agent contains an anti-tumor drug.

In the present disclosure, the anti-tumor drug is an anti-tumor drug known in the prior art, and when treating tumors, the first agent containing carrimycin and the pharmaceutically acceptable salts thereof can be used together with these anti-tumor agents. When the tumors are treated in combination, the first agent containing carrimycin and the pharmaceutically acceptable salts thereof may be used first, or the second agent containing the anti-tumor drug known in the prior art may be used first, or both are used simultaneously.

In the present disclosure, the anti-tumor drug is one or more than one drug selected from a group containing a chemotherapy drug, a radiotherapy drug, a targeted therapy drug, and an immunotherapeutic drug.

The present disclosure shows that the first agent containing carrimycin and the pharmaceutically acceptable salts thereof has a good therapeutic effect on various cancers including lung cancer, liver cancer, cervical cancer, etc., and the combination use of the first agent containing carrimycin and the pharmaceutically acceptable salts thereof with the anti-tumor drug known in the art such as cyclophosphamide, chlorambucil, nitrocaphane, lomustine, thio-TEPA, busulfan, and cisplatin can achieve synergistic effects and has a better therapeutic effect on tumor patients.

Patients with malignant tumors, subjected to various invasive procedures and anti-tumor drugs due to repeated treatments of radiotherapy, chemotherapy, surgery, and immunological preparations, have declined immunity as a whole, are at high risk of infections in the hospital, and can easily be infected in various ways. The analysis found that the nosocomial infection rate of tumor patients was significantly higher than that of discharged patients in the same hospital. The risk factors for nosocomial infection of tumor patients are mainly advanced age, long-term hospitalization, invasive operation and radiotherapy and chemotherapy, wherein radiotherapy and chemotherapy are the important special factor for impaired immunity of tumor patients. Due to the degenerative changes of the tissues and organs of the elderly patients, their immune defense function is reduced and their resistance is poor, accompanied with a variety of underlying diseases, and they are more likely to have nosocomial infections. Hospital stay and nosocomial infection are mutually causal, and as the length of hospital stay is extended, the chance of infection is increased.

Among all infections, respiratory infections are the most common, followed by skin infections, gastrointestinal infections and urinary tract infections. Blood infections are rare, but they are more dangerous and have high mortality. Relationship between a tumor site and an infection rate: although the incidence of lung, stomach and blood tumors is high, the infection rate is not the highest, about 20%; although there are fewer patients with pancreas, esophagus, hepatobiliary, and otolaryngology tumors, their infection rate is higher, accounting for 40% or above. The infection rates of breast cancer and thyroid cancer are all around 10%. Urinary system tumors have the lowest infection rate, only about 5%.

Infected pathogens mainly include Gram negative bacterial infections (about 45%-55%) and fungal infections (30% or above) (results based on the samples mainly from throat swabs and sputum specimens, etc.). Among Gram negative bacteria, *Escherichia coli, Klebsiella pneumoniae, Pseudomonas aeruginosa* and *Acinetobacter baumannii* are dominant. In some hospitals, fungal infections are the highest probably because the malignant tumor itself is a wasting disease, and the radiotherapy and chemotherapy and invasive operation inhibit the bone marrow hematopoietic function, weaken the defense ability of the body monocyte phagocytic system and destroy the immune barrier of the body. In addition, the extensive use of broad-spectrum antibacterial drugs and immunosuppressants can affect human protein metabolism, and even cause damage to the functions of liver and kidney and bone marrow, providing a possibility for fungi to evade or interfere with host defense, which is the main cause of the malignant tumor patients suffering from fungal infections.

The carrimycin of the present disclosure has an excellent anti-infective effect, is beneficial to help the patient to clear the infection and restore the immune function, thereby achieving a better therapeutic effect when combined with the anti-tumor drug.

In the present disclosure, the first agent containing carrimycin and the pharmaceutically acceptable salts thereof is a pharmaceutically acceptable dosage form, such as tablets, capsules, enteric-coated preparations, and injections, made of carrimycin and pharmaceutically acceptable adjuvants.

The adjuvants used and the preparation methods of the various formulations can be carried out in accordance with the prior art.

Further, a dose of the medicament is in a range from 5 to 1,500 mg; preferably in a range from 50 to 1,000 mg; more preferably in a range from 100 to 400 mg.

Alternatively, the dose of the first agent is in a range from 5 to 1,500 mg; preferably in a range from 50 to 1,000 mg; more preferably in a range from 100 to 400 mg.

The present disclosure shows by experiments that carrimycin and the pharmaceutically acceptable salts thereof show good antiproliferative activity on human breast cancer cells MCF-7 and MDA-MB-231, human hepatoma cells HepG2 or murine hepatoma cells $H_{22}$, human non-small cell lung cancer cells A549, human large cell lung cancer cells H460 and H1299, human renal clear cell adenocarcinoma cell 786-O, human renal cell adenocarcinoma cell 769-P, human glioma cell U251, human glioblastoma cell A172, human tissue lymphoma cell U937, human cervical cancer cell HeLa, human prostate cancer cell PC3, human pancreatic cancer cell PANC-1, human esophageal cancer cell TE-1, human gastric adenocarcinoma cell SGC7901, human colon cancer cell HT-29, and human promyelocytic leukemia cell HL-60, confirming that carrimycin can be used for the treatment of tumor or cancer diseases caused by these cells.

The present disclosure further demonstrates through in vivo experiments that carrimycin and the pharmaceutically acceptable salts thereof have obvious inhibitory effects on the growth of human breast cancer cells MCF-7 and MDA-MB-231, human hepatoma cells HepG2 or murine hepatoma cells $H_{22}$, human non-small cell lung cancer cells A549, human large cell lung cancer cells H460 and H1299, human renal clear cell adenocarcinoma cell 786-O, human renal cell adenocarcinoma cell 769-P, human glioma cell U251, human glioblastoma cell A172, human tissue lymphoma cell U937, human cervical cancer cell HeLa, human prostate cancer cell PC3, human pancreatic cancer cell PANC-1, human esophageal cancer cell TE-1, human gastric adenocarcinoma cell SGC7901, human colon cancer cell HT-29, and human promyelocytic leukemia cell HL-60.

At the same time, trials by a number of patients with various tumors or cancers indicate that carrimycin and the pharmaceutically acceptable salts thereof have good therapeutic effects on various tumors or cancers such as lung cancer, cervical cancer and uterine cancer.

In the present disclosure, the medicament can be prepared into various pharmaceutically acceptable dosage forms such as tablets and capsules through the conventional method in the art.

In the present disclosure, carrimycin is composed of a plurality of spiramycin derivatives, and its main active components are isovaleryl spiromycin I, II and III, wherein isovaleryl spiramycin (I+II+III) should be no less than 60%.

Further, in the carrimycin of the present disclosure, isovaleryl spiromycin III should be no less than 30%;

Further, the total content of the acylated spiromycin in the carrimycin of the present disclosure should be no less than 80%.

Further, the sum of other unknown components should be no more than 5.0%.

Further, the amount of spiramycin III in the carrimycin of the present disclosure should be no more than 1.0%.

The typical chromatogram of carrimycin also includes the peaks of (iso)butyryl spiromycin II and/or (iso)butyryl spiromycin III in addition to the peaks of isovaleryl spiromycin I, II and III.

Preferably, the typical chromatogram of carrimycin further comprises one or more selected from a group consisting of the peaks of spiramycin III, monoacetyl spiramycin II, monoacetyl spiramycin III, propionyl spiramycin II, propionyl spiromycin III, (iso)butyryl spiromycin II and (iso) butyryl spiromycin III.

The beneficial effects of the present disclosure are as follows: the present disclosure proves that carrimycin and the pharmaceutically acceptable salts thereof have good anti-tumor effects, especially have good curative effects on breast cancer, liver cancer, lung cancer, renal clear cell adenocarcinoma, renal cell adenocarcinoma, brain tumor, cervical cancer, prostate cancer, pancreatic cancer, esophageal cancer, gastric adenocarcinoma, colon cancer, lymphoma or leukemia and other tumors. The present disclosure not only provides a theoretical basis for the application and clinical promotion of carrimycin and the pharmaceutically acceptable salts thereof in the preparation of anti-tumor drugs, but also has important economic and social benefits.

BRIEF DESCRIPTION OF THE DRAWINGS

FIG. 1 is a photograph of tumors of each administration group in an in vivo test of the inhibitory effect of carrimycin on a human non-small cell lung cancer nude mouse model.

DETAILED DESCRIPTION OF THE EMBODIMENTS

To make the objectives, technical solutions and advantages of the embodiments of the present disclosure clearer, a clear and complete description of the technical solutions in the present embodiments will be given below, in combination with the embodiments of the present disclosure. The following embodiments are used to illustrate the present disclosure, but are not used to limit the protection scope of the present disclosure.

In the following embodiments, the carrimycin used is composed of a variety of spiramycin derivatives, and its main active components are isovaleryl spiromycin I, II and III, wherein isovaleryl spiramycin (I+II+III) should be no less than 60%.

Further, in the carrimycin of the present disclosure, isovaleryl spiromycin III should be no less than 30%;

Further, the total content of the acylated spiromycin in the carrimycin of the present disclosure should be no less than 80%.

Further, the sum of other unknown components should be no more than 5.0%.

Further, the amount of spiramycin III in the carrimycin of the present disclosure should be no more than 1.0%.

The typical chromatogram of carrimycin also includes the peaks of (iso)butyryl spiromycin II and/or (iso)butyryl spiromycin III in addition to the peaks of isovaleryl spiromycin I, II and III.

Preferably, the typical chromatogram of carrimycin further comprises one or more selected from a group consisting of the peaks of spiramycin III, monoacetyl spiramycin II, monoacetyl spiramycin III, propionyl spiramycin II, propionyl spiromycin III, (iso)butyryl spiromycin II and (iso) butyryl spiromycin III.

The following tests are also performed on different batches of carrimycin, and the results obtained are similar.

Embodiment 1 Carrimycin Tablets

Specification: 200 mg/350 mg
Tablet Core Prescription:

| Carrimycin | 200 g |
| Microcrystalline cellulose | 110 g |

-continued

| Sodium carboxymethyl starch | 22 g |
| Povidone $K_{30}$ (5%) | 15 g |
| Magnesium stearate | 3 g |
| Prepared into | 1,000 tablets |

Coating Liquid Prescription:

| Opadry II | 21 g |
| Distilled water | appropriate amount |
| Prepared into | 105 ml |

Preparation Process:

Preparation of the tablet core: the main drug and adjuvants respectively passed through a 100-mesh sieve, and a prescription amount of carrimycin, a prescription amount of microcrystalline cellulose and a ½ prescription amount of sodium carboxymethyl starch were uniformly mixed, and then a 5% povidone $K_{30}$ aqueous solution was added to make a soft material. A 18-mesh sieve was used for granulating, and the wet granules were dried under a ventilated condition at 60° C. for 2 hours. After the wet granules were dried, a 18-mesh sieve was used for dispersing the granules, and then a ½ prescription amount of sodium carboxymethyl starch and prescription amount of magnesium stearate were added. And after the materials were uniformly mixed, the mixture was tabletted with a shallow concave stamping die having a diameter of 11 mm to obtain a tablet core containing drugs, wherein the tablet is 350 mg in weight and 6.5 kg in hardness.

Preparation of the coating liquid: the required Opadry II (white) was weighed, the required amount of water was added into a liquid preparation container, the Opadry II was added into the liquid preparation container in batch. After all the Opadry II was added, the stirring speed was reduced to make the spiral disappear, and then stirring was continued to be performed for 30 min to obtain the coating liquid.

Preparation of thin film coated tablets: the tablet core was placed in a coating pan, the coating conditions were determined, and coating was carried out with the host speed of 20 r/min, the inlet air temperature of 40° C., the outlet air temperature of 30° C., the spray pressure of 0.02 Mpa, and the spray slurry flow rate of 1 ml/min. And after a constant state was achieved, the coating was continuously to be sprayed for 1.5 hours until the surfaces of the tablets were smooth and uniform in color, wherein tablets which were in compliance with the inspection standard of film coatings were qualified. The coating gains about 5% in weight.

Embodiment 2 Carrimycin Tablets (Calculated by 10,000 Tablets)

Prescription:

| Carrimycin raw powder | 1,000 g |
| Low-substituted hydroxypropyl cellulose (5%) | 92.5 g |
| Sodium carboxymethyl starch (3%) | 55.5 g |
| Magnesium stearate (1%) | 18.5 g |
| Starch | Total weight minus the weight of other raw and auxiliary materials |
| Total weight | 1,850 g |

Preparation process: an appropriate amount of starch was weighed, diluted to a concentration of 15%, and heated to a paste to get a binder; the main material carrimycin, and the adjuvants starch, low-substituted hydroxypropyl cellulose, sodium carboxymethyl starch, and magnesium stearate pass through a 100-mesh sieve, respectively, and the required main material and adjuvants were weighed according to the prescription amount. After the carrimycin, starch and low-substituted hydroxypropyl cellulose were fully and uniformly mixed, the starch paste with a starch concentration of 15% was used to prepare the mixture into a soft material which was granulated by a 14-mesh sieve, and granules were dried at 50-60° C. to control a water content to be 3-5%. A 14-mesh sieve was used for dispersing the granules, and then sodium carboxymethyl starch and magnesium stearate were added to be mixed, and the granule content was measured. The weight of the tablet was calculated according to the granule content, and the mixture was tabletted (with a 19 mm shallow concave punch), then the difference in the weight of the tablets was detected. After passing the test, the tablets were packaged.

Embodiment 3 Carrimycin Capsules (Calculated by 10,000 Granules)

Prescription:

| | |
|---|---|
| Carrimycin raw powder | 1,000 g |
| Starch (medicinal) | 1,080 minus the weight of carrimycin raw powder |
| No. 3 medicinal capsule | 1,000 granules |
| Liquid paraffin | 50 ml |

Preparation process: the main material carrimycin and the adjuvant medicinal starch were separately weighed according to the process formula amount, and then fully mixed in a mixer for 1.5-2 hours. The data obtained by sampling and content testing should be basically consistent with the theoretical data (the weight of each capsule was about 0.105 g), and the qualified No. 3 medicinal capsule and the mixed raw materials to be loaded were filled in a filling device according to the operation requirements of an automatic capsule machine, and the filled capsules were subjected to a difference test (±10% or less, <0.3 g) to see if the dissolution rate meets the requirements or not. The capsules that meet the requirements after being tested were put into a polishing machine to be polished for 15-20 minutes with the liquid paraffin added, and then were taken out to be tested by finished product packaging boxes.

Embodiment 4 Carrimycin Dry Syrup (Calculated According to 10,000 Bags)

Prescription:

| | |
|---|---|
| Carrimycin raw powder | 1,250 g |
| Citric acid (0.5%) | 15 g |
| Sucrose | total weight minus other raw and auxiliary materials |
| Total weight | about 500 g |
| Pigment (curcumin) | about 1 g |

Preparation process: the carrimycin raw powder, citric acid and sucrose were respectively grinded into granules by a high-speed jet mill, and 85% of the granules pass through a 300-mesh sieve, 15% of the granules pass through a 180-mesh sieve. Then the fine powder after grinding was weighed according to the prescription amount and fully mixed for 1-1.5 hours, the content was measured, the loading capacity was calculated (the theoretical loading capacity was 500 mg per bag). Then the mixture was put into a bagging machine, aluminum foil paper was installed, and filling was carried out according to the operation requirements of a filling machine. The difference was allowed to be within ±5%, and after the filling, the outer packaging was carried out after passing the inspection.

Embodiment 5 Carrimycin Granules (Calculated According to 10,000 Bags)

Prescription:

| | |
|---|---|
| Carrimycin raw powder | 1,250 g |
| Powdered sugar | 20,000 g |
| Dextrin | 9,000 g |
| 5% PVP-$K_{30}$ | appropriate amount |

Preparation process: the carrimycin raw powder, the powdered sugar and the dextrin pass through a 120-mesh sieve, and the carrimycin, powdered sugar and dextrin were weighed according to the prescription amount and uniformly mixed. And the above uniformly mixed materials were made into a soft material with a 5% PVP-K30 mucilage, and then the soft material was granulated with a swinging granulation machine, dried at 70° C. and subjected to granule dispersion, and the resulting granules were subpackaged after being qualified for inspection.

Embodiment 6 Carrimycin Freeze-Dried Powder Injection 500 mg of carrimycin raw powder was uniformly mixed with an equimolar amount of propylene glycol, and the mixture was dissolved in 5 ml of water to obtain a faint yellow clear solution having a pH between 4.6 and 5.6. Further, 40 mg of mannitol was added as a lyophilized proppant into the faint yellow clear solution, and after being frozen rapidly at a low temperature for 9 hours, the material was freeze-dried to obtain a faint yellow loose mass, which was dissolved in 10 ml of sterile water before being used.

Test Example 1 Bioassay of Anti-Tumor Activity

The purpose of the assay is to evaluate the in vitro cell proliferation inhibition or cytotoxic activity of a tested sample.

Cell Strains:

Human breast cancer cells MCF-7 and MDA-MB-231, human hepatoma cells HepG2, human non-small cell lung cancer cells A549, human large cell lung cancer cells H460 and H1299, human renal clear cell adenocarcinoma cell 786-O, human renal cell adenocarcinoma cell 769-P, human glioma cell U251, human glioblastoma cell A172, human tissue lymphoma cell U937, human cervical cancer cell HeLa, human prostate cancer cell PC3, human pancreatic cancer cell PANC-1, human esophageal cancer cell TE-1, human gastric adenocarcinoma cell SGC7901, human colon cancer cell HT-29, and human promyelocytic leukemia cell HL-60.

Reagents:

RPMI1640 medium, MEM medium, DMEM low sugar medium, fetal calf serum purchased from Gibco, USA, trypsin, glutamine, penicillin, streptomycin, dimethyl sulfoxide (DMSO), and methyl-thiazol-tetrazolium (MTT) purchased from Sigma, USA.

Instruments:

Carbon dioxide incubator (Sanyo, Japan), enzyme-linked immunosorbent analyzer (Tecan, Austria), 96-well culture plate (Corning, USA), inverted microscope (Motic, China).

The operation steps are as follows:

Adherent Cells:

MCF-7, MDA-MB-231, HepG2, A549, H460, H1299, 786-O, 769-P, U251, A172, HeLa, PC3, PANC-1, TE-1, SGC7901, and HT-29 are adherent tumor cells. The adherent tumor cells in the logarithmic growth phase were selected and digested with trypsin, then were prepared into a 4 to $5\times10^4$/ml cell suspension by a medium containing 10% fetal bovine serum. And the cell suspension was inoculated in a 96-well culture plate, and each well was 100 μL. The 96-well culture plate was cultured at 37° C. and 5% $CO_2$ for 24 hours. The experimental group was replaced with a new culture medium containing different concentrations of the sample to be tested, namely carrimycin, while the control group was replaced with a culture medium containing the same volume of solvent. And each group was set up with 3 parallel wells that were cultured at 37° C. and 5% $CO_2$ for 48 hours. After the supernatant was removed, the wells were washed carefully for 3 times with PBS. And 100 μL of freshly prepared culture medium containing 0.5 mg/ml MTT was added to each well for continuous incubation for 4 hours at 37° C. After the supernatant was removed carefully, 150 μL of DMSO was added to each well, and after the material was mixed for 10 minutes with a micro-oscillator, the optical density value was measured at 492 nm with a microplate reader.

Suspension Cells:

U937 and HL-60 were suspension cells. And cells in a logarithmic growth phase were selected and prepared into a $2\times10^5$/ml cell suspension by a RPMI 1640 culture medium containing 10% fetal bovine serum. And the cell suspension was inoculated in a 96-well culture plate, and each well was 50 μL. The 96-well culture plate was cultured at 37° C. and 5% $CO_2$ for 24 hours. 50 μL of a culture medium containing different concentrations of the tested sample carrimycin was added in the experimental group, while a culture medium containing the same volume of solvent was added into the control group. Each group was set up with 3 parallel wells that were cultured at 37° C. and 5% $CO_2$ for 48 h. And 10 μL of freshly prepared medium containing 5 mg/ml MTT was added into each well for continuous incubation for 4 hours at 37° C. The crystals were dissolved in 100 μL of a triple solution (SDS 10 g, 10 M HCl 0.1 mL, isobutanol 5 mL, diluted with distilled water to 100 mL), and incubated at 37° C. for 12 hours. The optical density value was measured at 492 nm with a microplate reader.

Evaluation of Results:

The inhibition rate of the medicament on tumor cell growth is calculated according to the following formula:

Tumor cell growth inhibition rate (%)=[$A_{492}$ (negative control)–$A_{492}$ (dosing group)]/$A_{492}$ (negative control)×100%

And the half-inhibitory concentration ($IC_{50}$) of the sample is determined therefrom.

Results:

The evaluation results of in vitro antiproliferative activity of the samples selected from human breast cancer cells MCF-7 and MDA-MB-231, human hepatoma cells HepG2, human non-small cell lung cancer cells A549, human large cell lung cancer cells H460 and H1299, human renal clear cell adenocarcinoma cell 786-O, human renal cell adenocarcinoma cell 769-P, human glioma cell U251, human glioblastoma cell A172, human tissue lymphoma cell U937, human cervical cancer cell HeLa, human prostate cancer cell PC3, human pancreatic cancer cell PANC-1, human esophageal cancer cell TE-1, human gastric adenocarcinoma cell SGC-7901, human colon cancer cell HT-29, and human promyelocytic leukemia cell HL-60 are shown in Table 1:

TABLE 1

Inhibition of carrimycin on the proliferation of tumor cells

| Cell Strain | $IC_{50}$ (μg/mL) | Cell Strain | $IC_{50}$ (μg/mL) |
|---|---|---|---|
| MCF-7 | 11.2 ± 1.5 | A172 | 11.2 ± 2.0 |
| MDA-MB-231 | 14.8 ± 1.0 | U937 | 12.4 ± 0.8 |
| HepG2 | 8.8 ± 2.7 | HeLa | 11.9 ± 2.8 |
| A549 | 15.4 ± 2.1 | PC3 | 7.4 ± 2.4 |
| H460 | 7.7 ± 0.9 | PANC-1 | 9.1 ± 1.3 |
| H1299 | 12.7 ± 1.7 | TE-1 | 7.8 ± 2.1 |
| 786-O | 18.0 ± 2.5 | SGC-7901 | 8.2 ± 1.6 |
| 769-P | 7.6 ± 3.7 | HT-29 | 12.1 ± 2.7 |
| U251 | 6.9 ± 1.2 | HL-60 | 17.5 ± 1.7 |

The available results show that the samples show good anti-proliferative activity against the cells tested.

Test Example 2 In Vivo Test

1. Inhibition of Carrimycin on Human Non-Small Cell Lung Cancer in Nude Mice Model Establishment of a Mouse Solid Tumor Model A549 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1\times10^7$/ml with matrigel, then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group. And carrimycin doses of 12.5, 25 and 50 mg/kg were given to 3 groups, respectively. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein V=a×b²/2; RTV=V/$V_0$ ($V_0$ is the tumor volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see FIG. 1, Table 2, and Table 3).

The tumor growth inhibition rates of carrimycin groups with low, medium and high doses of carrimycin are 54.46%, 66.07% and 75.89%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 54.55%, 45.57% and 29.21%, respectively.

There are no significant changes in the mouse weight of carrimycin groups with low, medium and high doses of carrimycin compared with the model group.

mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V=a \times b^2/2$; $RTV=V/V_0$ ($V_0$ is the tumor volume before administration, V is the tumor volume before sacrifice), and T/C (%)=treatment group RTV/model control group RTV×100%.

TABLE 2

Effect of carrimycin on the inhibition rate of transplanted tumor of human non-small cell lung cancer A549 cells in nude mice ($\bar{x} \pm s$)

| Group | Dose (mg/kg) | Number of Animals (Start/End) | Body Weight (g)(d$_1$) | Body Weight (g)(d$_{30}$) | Tumor Weight (g) | Inhibition Rate(%) |
|---|---|---|---|---|---|---|
| Model Group | 0 | 6/6 | 20.27 ± 0.82 | 19.71 ± 1.48 | 1.12 ± 0.37 | — |
| Cyclophosphamide | 30 | 6/6 | 20.89 ± 0.91 | 18.97 ± 0.82 | 0.21 ± 0.11*** | 81.25 |
| Carrimycin | 12.5 | 6/6 | 21.01 ± 1.23 | 19.22 ± 1.91 | 0.51 ± 0.18* | 54.46 |
|  | 25 | 6/6 | 20.79 ± 0.84 | 19.74 ± 1.67 | 0.38 ± 0.24** | 66.07 |
|  | 50 | 6/6 | 21.00 ± 2.12 | 19.61 ± 1.72 | 0.27 ± 0.17** | 75.89 |

*$p < 0.05$ compared with the model group,
**$p < 0.01$ compared with the model group,
***$p < 0.001$ compared with the model group

TABLE 3

Effect of carrimycin on the volume change of transplanted tumor of human non-small cell lung cancer A549 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 129.51 ± 16.24 | 2208.17 ± 196.71 | 17.05 ± 0.72 | — |
| Cyclophosphamide | 30 | 6/6 | 127.26 ± 15.21 | 504.75 ± 143.63* | 3.97 ± 0.68** | 23.28 |
| Carrimycin | 12.5 | 6/6 | 127.15 ± 13.23 | 1182.75 ± 121.77* | 9.30 ± 1.25* | 54.55 |
|  | 25 | 6/6 | 125.62 ± 15.20 | 975.71 ± 118.12* | 7.77 ± 0.38** | 45.57 |
|  | 50 | 6/6 | 129.21 ± 13.48 | 643.52 ± 124.76** | 4.98 ± 0.29*** | 29.21 |

*$p < 0.05$ compared with the model group;
**$p < 0.01$ compared with the model group,
***$p < 0.001$ compared with the model group 2. Inhibition of Carrimycin on Human Breast Cancer in Nude Mice Model Establishment of a Mouse Solid Tumor Model MCF-7 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, and then each nude mouse was inoculated subcutaneously with 0.2 ml of cells at its right armpit and recorded as the first day of inoculation. When the tumor growed to be greater than or equal to 100 mm$^3$, the Calculation of Tumor Growth Inhibition Rate Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 4, and Table 5).

The tumor growth inhibition rates of carrimycin groups with low, medium and high doses of carrimycin are 11.73%, 25.13% and 45.55%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 57.37%, 47.65% and 33.46%, respectively.

There are no significant changes in the mouse weight of carrimycin groups with low, medium and high doses of carrimycin compared with the model group.

for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V = a \times b^2/2$; $RTV = V/V_0$ ($V_0$ is the tumor volume before administration, V is the tumor volume before

TABLE 4

Effect of carrimycin on the inhibition rate of transplanted tumor of human breast cancer MCF-7 cells in nude mice ($\bar{x} \pm s$)

| Group | Dose (mg/kg) | Number of Animals (Start/End) | Body Weight (g)($d_1$) | Body Weight (g)($d_{30}$) | Tumor Weight (g) | Inhibition Rate (%) |
|---|---|---|---|---|---|---|
| Model Group | 0 | 6/6 | 22.10 ± 0.37 | 20.59 ± 0.95 | 1.91 ± 0.15 | — |
| Cyclophosphamide | 30 | 6/6 | 21.93 ± 0.89 | 19.79 ± 1.47 | 0.72 ± 0.21*** | 62.3 |
| Carrimycin | 12.5 | 6/6 | 20.01 ± 0.88 | 19.02 ± 1.73 | 1.69 ± 0.17* | 11.73 |
|  | 25 | 6/6 | 21.79 ± 1.04 | 19.97 ± 1.18 | 1.43 ± 0.16*** | 25.13 |
|  | 50 | 6/6 | 20.82 ± 1.28 | 19.06 ± 0.94 | 1.04 ± 0.17*** | 45.55 |

*$p < 0.05$ compared with the model group,
**$p < 0.01$ compared with the model group,
***$p < 0.001$ compared with the model group

TABLE 5

Effect of carrimycin on the volume change of transplanted tumor of human breast cancer MCF-7 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 128.31 ± 18.44 | 2098.34 ± 119.32 | 16.35 ± 0.58 | — |
| Cyclophosphamide | 30 | 6/6 | 127.68 ± 14.89 | 638.62 ± 123.11** | 5.00 ± 1.27** | 30.58 |
| Carrimycin | 12.5 | 6/6 | 128.02 ± 13.61 | 1200.47 ± 101.49* | 9.38 ± 0.66* | 57.37 |
|  | 25 | 6/6 | 126.28 ± 17.31 | 983.64 ± 127.72* | 7.79 ± 0.63*** | 47.65 |
|  | 50 | 6/6 | 128.58 ± 13.48 | 703.52 ± 119.94** | 5.47 ± 0.74*** | 33.46 |

*$p < 0.05$ compared with the model group;
**$p < 0.01$ compared with the model group,
***$p < 0.001$ compared with the model group 3. Inhibition of Carrimycin on Human Lymphoma in Nude Mice Model Establishment of a Mouse Solid Tumor Model U937 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, and then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 6, and Table 7).

The tumor growth inhibition rates of carrimycin groups with low, medium and high doses of carrimycin are 61.08%, 65.94% and 70.50%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 52.37%, 47.31% and 39.95%, respectively.

There are no significant changes in the mouse weight of carrimycin groups with low, medium and high doses of carrimycin compared with the model group.

the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V=a\times b^2/2$; $RTV=V/V_0$ ($V_0$ is the tumor volume before administration, V is the tumor volume before

TABLE 6

Effect of carrimycin on the inhibition rate of transplanted tumor of human lymphoma U937 cells in nude mice ($\bar{x} \pm s$)

| Group | Dose (mg/kg) | Number of Animals (Start/End) | Body Weight (g)($d_1$) | Body Weight (g)($d_{30}$) | Tumor Weight (g) | Inhibition Rate (%) |
|---|---|---|---|---|---|---|
| Model Group | 0 | 6/6 | 19.04 ± 0.60 | 18.79 ± 0.68 | 1.75 ± 0.12 | — |
| Cyclophosphamide | 30 | 6/6 | 19.79 ± 0.86 | 18.85 ± 0.62 | 0.38 ± 0.16*** | 78.40 |
| Carrimycin | 12.5 | 6/6 | 18.83 ± 1.01 | 18.03 ± 0.78 | 0.68 ± 0.13*** | 61.08 |
|  | 25 | 6/6 | 19.57 ± 0.72 | 18.62 ± 1.32 | 0.60 ± 0.15*** | 65.94 |
|  | 50 | 6/6 | 18.97 ± 1.47 | 17.94 ± 1.59 | 0.52 ± 0.13*** | 70.50 |

*p < 0.05 compared with the model group,
**p < 0.01 compared with the model group,
***p < 0.001 compared with the model group

TABLE 7

Effect of carrimycin on the volume change of transplanted tumor of human lymphoma U937 cells in nude mice ($\bar{x} \pm s$)

| Group | Dose (mg/kg) | Number of Animals (Start/End) | Tumor Volume (mm³) ($d_1$) | Tumor Volume (mm³) ($d_{30}$) | Relative Tumor Volume (RTV) | Relative Tumor Proliferation Rate(T/C) |
|---|---|---|---|---|---|---|
| Model Group | 0 | 6/6 | 140.04 ± 15.73 | 2600.94 ± 217.73 | 18.57 ± 1.03 | — |
| Cyclophosphamide | 30 | 6/6 | 139.58 ± 11.25 | 889.72 ± 59.73*** | 6.37 ± 0.94** | 34.30 |
| Carrimycin | 12.5 | 6/6 | 139.79 ± 10.94 | 1360.16 ± 198.71** | 9.73 ± 1.21** | 52.37 |
|  | 25 | 6/6 | 140.27 ± 13.66 | 1232.97 ± 239.55*** | 8.79 ± 0.48*** | 47.31 |
|  | 50 | 6/6 | 139.95 ± 12.51 | 1038.43 ± 124.81*** | 7.42 ± 0.61*** | 39.95 |

*p < 0.05 compared with the model group;
**p < 0.01 compared with the model group,
***p < 0.001 compared with the model group 4. Inhibition of Carrimycin on Human Cervical Cancer in Nude Mice Model Establishment of a Mouse Solid Tumor Model HeLa cells in a logarithmic growth phase were taken and subjected to a trypan blue exclusion experiment showing that the cell viability was more than 95%. Then the cells were subjected to trypsinization, centrifugation, and supernatant removal. Then cell concentration was adjusted to $1\times10^7$/ml with matrigel, then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of sacrifice), and T/C (%)=treatment group RTV/model control group RTV×100%.

Calculation of Tumor Growth Inhibition Rate Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)= (1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 8, and Table 9).

The tumor growth inhibition rates of carrimycin groups with low, medium and high doses of carrimycin are 28.75%, 46.28% and 56.18%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 61.04%, 53.27% and 40.40%, respectively.

There are no significant changes in the mouse weight of carrimycin groups with low, medium and high doses of carrimycin compared with the model group.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V=a \times b^2/2$; $RTV=V/V_0$ ($V_0$ is the tumor volume before administration, V is the tumor volume before

TABLE 8

Effect of carrimycin on the inhibition rate of transplanted tumor of human cervical cancer HeLa cells in nude mice ($\bar{x} \pm s$)

| Group | Dose (mg/kg) | Number of Animals (Start/End) | Body Weight (g)($d_1$) | Body Weight (g)($d_{30}$) | Tumor Weight (g) | Inhibition Rate (%) |
|---|---|---|---|---|---|---|
| Model Group | 0 | 6/6 | 20.82 ± 1.16 | 19.04 ± 0.69 | 1.78 ± 0.24 | — |
| Cyclophosphamide | 30 | 6/6 | 20.04 ± 0.68 | 19.20 ± 0.18 | 0.49 ± 0.39*** | 72.48 |
| Carrimycin | 12.5 | 6/6 | 20.89 ± 1.01 | 19.68 ± 1.31 | 1.26 ± 0.33* | 28.75 |
|  | 25 | 6/6 | 21.02 ± 0.71 | 19.92 ± 1.37 | 0.95 ± 0.4** | 46.28 |
|  | 50 | 6/6 | 20.96 ± 1.79 | 18.82 ± 0.74 | 0.78 ± 0.42** | 56.18 |

*p < 0.05 compared with the model group,
**p < 0.01 compared with the model group,
***p < 0.001 compared with the model group

TABLE 9

Effect of carrimycin on the volume change of transplanted tumor of human cervical cancer HeLa cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 116.31 ± 14.71 | 1643.16 ± 287.92 | 14.13 ± 0.62 | — |
| Cyclophosphamide | 30 | 6/6 | 115.78 ± 10.58 | 397.88 ± 103.60*** | 3.44 ± 0.93*** | 24.35 |
| Carrimycin | 12.5 | 6/6 | 112.67 ± 18.59 | 971.22 ± 136.48*** | 8.62 ± 0.58** | 61.04 |
|  | 25 | 6/6 | 117.53 ± 12.31 | 885.00 ± 238.58* | 7.53 ± 1.01* | 53.27 |
|  | 50 | 6/6 | 116.74 ± 13.48 | 666.59 ± 231.53* | 5.71 ± 0.79** | 40.40 |

*p < 0.05 compared with the model group;
**p < 0.01 compared with the model group,
***p < 0.001 compared with the model group 5. Inhibition of Carrimycin on Human Prostate Cancer in Nude Mice Model Establishment of a Mouse Solid Tumor Model PC3 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, and then each nude mouse was inoculated subcutaneously with 0.2 ml of cells at its right armpit and recorded as the first day of inoculation. When the tumor growed to be greater than or equal to 100 mm$^3$, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 10, and Table 11).

The tumor growth inhibition rates of carrimycin groups with low, medium and high doses of carrimycin are 25.92%, 34.67% and 60.32%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 55.93%, 43.45% and 30.02%, respectively.

There are no significant changes in the mouse weight of carrimycin groups with low, medium and high doses of carrimycin compared with the model group.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V=a \times b^2/2$; $RTV=V/V_0$ ($V_0$ is the tumor volume before administration, V is the tumor volume before

TABLE 10

Effect of carrimycin on the inhibition rate of transplanted tumor of human prostate cancer PC3 cells in nude mice ($\bar{x} \pm s$)

| Group | Dose (mg/kg) | Number of Animals (Start/End) | Body Weight (g)($d_1$) | Body Weight (g)($d_{30}$) | Tumor Weight (g) | Inhibition Rate (%) |
|---|---|---|---|---|---|---|
| Model Group | 0 | 6/6 | 18.95 ± 0.54 | 16.04 ± 0.61 | 1.87 ± 0.36 | — |
| Cyclophosphamide | 30 | 6/6 | 19.32 ± 0.25 | 18.68 ± 1.21 | 0.56 ± 0.4*** | 70.06 |
| Carrimycin | 12.5 | 6/6 | 19.02 ± 0.84 | 17.89 ± 0.68 | 1.38 ± 0.49* | 25.92 |
|  | 25 | 6/6 | 18.89 ± 1.03 | 17.93 ± 1.05 | 1.22 ± 0.48* | 34.67 |
|  | 50 | 6/6 | 19.25 ± 0.94 | 18.01 ± 0.57 | 0.74 ± 0.47** | 60.32 |

*$p < 0.05$ compared with the model group,
**$p < 0.01$ compared with the model group,
***$p < 0.001$ compared with the model group

TABLE 11

Effect of carrimycin on the volume change of transplanted tumor of human prostate cancer PC3 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 109.47 ± 8.99 | 2194.79 ± 169.54 | 20.05 ± 0.23 | — |
| Cyclophosphamide | 30 | 6/6 | 108.68 ± 13.62 | 507.88 ± 87.93** | 4.67 ± 0.82*** | 23.29 |
| Carrimycin | 12.5 | 6/6 | 109.16 ± 14.88 | 1223.68 ± 117.49* | 11.21 ± 0.77* | 55.93 |
|  | 25 | 6/6 | 107.35 ± 136 | 935.02 ± 182.67** | 8.71 ± 1.36** | 43.45 |
|  | 50 | 6/6 | 109.02 ± 18.31 | 682.43 ± 147.28** | 6.02 ± 1.02** | 30.02 |

*$p < 0.05$ compared with the model group;
**$p < 0.01$ compared with the model group,
***$p < 0.001$ compared with the model group 6. Inhibition of Carrimycin on Human Colon Cancer in Nude Mice Model Establishment of a Mouse Solid Tumor Model HT-29 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 12, and Table 13).

The tumor growth inhibition rates of carrimycin groups with low, medium and high doses of carrimycin are 40.55%, 60.68% and 73.16%, respectively.

The tumor volume and relative tumor volume of carrimycin groups with low, medium and high doses of carrimycin are significantly lower than those of the model group (P<0.05).

The relative tumor proliferation rates of carrimycin groups with low, medium and high doses of carrimycin are 49.31%, 42.30% and 30.96%, respectively.

There are no significant changes in the mouse weight of carrimycin groups with low, medium and high doses of carrimycin compared with the model group.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V = a \times b^2/2$; $RTV = V/V_0$ ($V_0$ is the tumor volume before administration, V is the tumor volume before

TABLE 12

Effect of carrimycin on the inhibition rate of transplanted tumor of human colon cancer HT-29 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 24.21 ± 02.27 | 23.93 ± 1.29 | 1.23 ± 0.13 | — |
| Cyclophosphamide | 30 | 6/6 | 23.76 ± 01.11 | 21.52 ± 01.32 | 0.40 ± 0.03** | 67.38 |
| Carrimycin | 12.5 | 6/6 | 22.03 ± 01.23 | 19.70 ± 01.78 | 0.73 ± 0.06* | 40.55 |
|  | 25 | 6/6 | 21.72 ± 01.96 | 20.97 ± 01.75 | 0.48 ± 0.19* | 60.68 |
|  | 50 | 6/6 | 21.83 ± 01.92 | 20.47 ± 01.32 | 0.33 ± 0.14** | 73.16 |

*p < 0.05 compared with the model group;
**p < 0.01 compared with the model group,

TABLE 13

Effect of carrimycin on the volume change of transplanted tumor of human colon cancer HT-29 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 138.57 ± 3.99 | 2808.57 ± 57.26 | 20.27 ± 1.21 | — |
| Cyclophosphamide | 30 | 6/6 | 156.61 ± 5.92 | 816.17 ± 21.03*** | 5.21 ± 0.70*** | 25.71 |
| Carrimycin | 12.5 | 6/6 | 152.38 ± 9.45 | 1523.10 ± 42.71* | 10.00 ± 0.38** | 49.31 |
|  | 25 | 6/6 | 158.48 ± 7.91 | 1358.77 ± 74.69** | 8.57 ± 3.16** | 42.30 |
|  | 50 | 6/6 | 156.01 ± 7.06 | 978.85 ± 68.35*** | 6.27 ± 2.74*** | 30.96 |

*p < 0.05 compared with the model group;
**p < 0.01 compared with the model group,
***p < 0.001 compared with the model group 7. Inhibition of Carrimycin on Human Leukemia in Nude Mice Model Establishment of a Mouse Solid Tumor Model HL-60 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, and then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 14, and Table 15).

The tumor growth inhibition rates of carrimycin groups with low, medium and high doses of carrimycin are 40.26%, 70.92% and 83.35%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 58.63%, 49.26% and 38.33%, respectively.

There are no significant changes in the mouse weight of carrimycin groups with low, medium and high doses of carrimycin compared with the model group.

TABLE 14

Effect of carrimycin on the inhibition rate of transplanted tumor of human leukemia HL-60 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 23.21 ± 1.27 | 22.93 ± 1.23 | 8.11 ± 0.93 | — |
| Cyclophosphamide | 30 | 6/6 | 22.66 ± 1.11 | 20.52 ± 1.73 | 1.46 ± 0.24*** | 81.37 |
| Carrimycin | 12.5 | 6/6 | 20.38 ± 1.47 | 18.70 ± 1.21 | 4.76 ± 0.54* | 40.26 |
|  | 25 | 6/6 | 21.72 ± 1.74 | 20.97 ± 1.83 | 2.20 ± 0.36*** | 70.92 |
|  | 50 | 6/6 | 22.03 ± 1.94 | 20.47 ± 1.43 | 1.35 ± 0.178*** | 83.35 |

*$p < 0.05$ compared with the model group,
**$p < 0.01$ compared with the model group,
***$p < 0.001$ compared with the model group,

TABLE 15

Effect of carrimycin on the volume change of transplanted tumor of human leukemia HL-60 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 243.02 ± 77.53 | 2803.14 ± 288.94 | 11.53 ± 3.23 |  |
| Cyclophosphamide | 30 | 6/6 | 209.22 ± 50.12 | 1415.16 ± 320.21 | 6.76 ± 2.53*** | 58.63 |
| Carrimycin | 12.5 | 6/6 | 296.41 ± 80.12 | 2088.26 ± 324.12 | 7.05 ± 0.24* | 61.14 |
|  | 25 | 6/6 | 253.31 ± 74.92 | 1438.94 ± 242.32 | 5.68 ± 1.32*** | 49.26 |
|  | 50 | 6/6 | 215.68 ± 68.96 | 954.04 ± 132.43 | 4.42 ± 3.86*** | 38.33 |

*$p < 0.05$ compared with the model group;
**$p < 0.01$ compared with the model group,
***$p < 0.001$ compared with the model group 8. Inhibition of Carrimycin on Human Hepatocarcinoma in Nude Mice Model Establishment of a Mouse Solid Tumor Model HepG-2 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1\times10^7$/ml with matrigel, and then each nude mouse was inoculated subcutaneously with 0.2 ml of cells at its right armpit and recorded as the first day of inoculation. When the tumor growed to be greater than or equal to 100 mm$^3$, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V=a\times b^2/2$; $RTV=V/V_0$ ($V_0$ is the tumor volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 16, and Table 17).

The tumor growth inhibition rates of carrimycin groups with low, medium and high doses of carrimycin are 37.79%, 51.92% and 61.11%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 65.55%, 53.58% and 39.33%, respectively.

There are no significant changes in the mouse weight of carrimycin groups with low, medium and high doses of carrimycin compared with the model group.

TABLE 16

Effect of carrimycin on the inhibition rate of transplanted tumor of human hepatocarcinoma HepG-2 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 22.21 ± 1.77 | 20.93 ± 1.26 | 1.26 ± 0.17 | — |
| Cyclophosphamide | 30 | 6/6 | 22.67 ± 1.54 | 21.52 ± 1.99 | 0.46 ± 0.07*** | 63.48 |
| Carrimycin | 12.5 | 6/6 | 19.64 ± 0.97 | 18.36 ± 0.92 | 0.79 ± 0.04* | 37.79 |
|  | 25 | 6/6 | 23.24 ± 1.43 | 21.97 ± 1.76 | 0.61 ± 0.12** | 51.92 |
|  | 50 | 6/6 | 22.65 ± 2.09 | 20.88 ± 1.63 | 0.49 ± 0.11** | 61.11 |

*$p < 0.05$ compared with the model group;
**$p < 0.01$ compared with the model group,
***$p < 0.001$ compared with the model group

TABLE 17

Effect of carrimycin on the volume change of transplanted tumor of human hepatocarcinoma HepG-2 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 155.33 ± 9.12 | 2036.45 ± 68.79 | 13.12 ± 0.43 | — |
| Cyclophosphamide | 30 | 6/6 | 146.12 ± 2.30 | 623.67 ± 28.44*** | 4.27 ± 0.26*** | 32.55 |
| Carrimycin | 12.5 | 6/6 | 144.00 ± 2.10 | 1239.30 ± 7.75** | 8.60 ± 0.07** | 65.55 |
|  | 25 | 6/6 | 145.75 ± 1.31 | 1025.85 ± 14.84** | 7.04 ± 0.05** | 53.58 |
|  | 50 | 6/6 | 157.76 ± 2.30 | 813.70 ± 30.50** | 5.16 ± 0.07** | 39.33 |

*$p < 0.05$ compared with the model group;
**$p < 0.01$ compared with the model group,
***$p < 0.001$ compared with the model group 9. Inhibition of Carrimycin on Human Breast Cancer in Nude Mice Model Establishment of a Mouse Solid Tumor Model MDA-MB-231 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1\times10^7$/ml with matrigel, and then each nude mouse was inoculated subcutaneously with 0.2 ml of cells at its right armpit and recorded as the first day of inoculation. When the tumor growed to be greater than or equal to 100 mm$^3$, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V=a\times b^2/2$; $RTV=V/V_0$ ($V_0$ is the tumor volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 18, and Table 19).

The tumor growth inhibition rates of carrimycin groups with low, medium and high doses of carrimycin are 46.96%, 58.88% and 72.55%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 59.42%, 48.69% and 35.78%, respectively.

There are no significant changes in the mouse weight of carrimycin groups with low, medium and high doses of carrimycin compared with the model group.

TABLE 18

Effect of carrimycin on the inhibition rate of transplanted tumor of human breast cancer MDA-MB-231 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 20.42 ± 1.87 | 18.77 ± 0.79 | 1.34 ± 0.22 | — |
| Cyclophosphamide | 30 | 6/6 | 21.28 ± 0.95 | 19.79 ± 1.03 | 0.27 ± 0.11*** | 79.75 |
| Carrimycin | 12.5 | 6/6 | 20.88 ± 0.89 | 18.47 ± 0.75 | 0.71 ± 0.09*** | 46.96 |
|  | 25 | 6/6 | 21.79 ± 1.79 | 19.72 ± 0.69 | 0.55 ± 0.14* | 58.88 |
|  | 50 | 6/6 | 21.01 ± 0.85 | 19.68 ± 1.14 | 0.37 ± 0.13* | 72.55 |

*$p < 0.05$ compared with the model group;
**$p < 0.01$ compared with the model group,
***$p < 0.001$ compared with the model group

TABLE 19

Effect of carrimycin on the volume change of transplanted tumor of human breast cancer MDA-MB-231 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 173.69 ± 8.47 | 2101.58 ± 32.69 | 12.10 ± 0.94 | — |
| Cyclophosphamide | 30 | 6/6 | 169.73 ± 11.79 | 587.27 ± 30.47* | 3.46 ± 0.70* | 28.59 |
| Carrimycin | 12.5 | 6/6 | 170.58 ± 9.94 | 1226.47 ± 26.53** | 7.19 ± 0.41** | 59.42 |
|  | 25 | 6/6 | 172.68 ± 9.59 | 1017.09 ± 42.64* | 5.89 ± 1.37* | 48.69 |
|  | 50 | 6/6 | 171.62 ± 7.06 | 743.11 ± 68.35*** | 4.33 ± 1.68** | 35.78 |

*$p < 0.05$ compared with the model group;
**$p < 0.01$ compared with the model group,
***$p < 0.001$ compared with the model group 10. Inhibition of Carrimycin on Human Large Cell Lung Cancer in Nude Mice Model Establishment of a Mouse Solid Tumor Model H460 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1\times10^7$/ml with matrigel, and then each nude mouse was inoculated subcutaneously with 0.2 ml of cells at its right armpit and recorded as the first day of inoculation. When the tumor growed to be greater than or equal to 100 mm$^3$, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V=a\times b^2/2$; $RTV=V/V_0$ ($V_0$ is the tumor volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 20, and Table 21).

The tumor growth inhibition rates of carrimycin groups with low, medium and high doses of carrimycin are 37.79%, 51.92% and 61.11%, respectively.

The tumor volume and relative tumor volume of carrimycin groups with low, medium and high doses of carrimycin are significantly lower than those of the model group (P<0.05).

The relative tumor proliferation rates of carrimycin groups with low, medium and high doses of carrimycin are 73.83%, 61.83% and 49.82%, respectively.

There are no significant changes in the mouse weight of carrimycin groups with low, medium and high doses of carrimycin compared with the model group.

TABLE 20

Effect of carrimycin on the inhibition rate of transplanted tumor of human large cell lung cancer H460 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 19.57 ± 0.94 | 18.47 ± 0.24 | 1.95 ± 0.16 | — |
| Cyclophosphamide | 30 | 6/6 | 20.32 ± 0.87 | 19.25 ± 0.83 | 0.61 ± 0.13*** | 68.49 |
| Carrimycin | 12.5 | 6/6 | 19.97 ± 1.02 | 18.38 ± 1.37 | 1.40 ± 0.25** | 37.79 |
|  | 25 | 6/6 | 20.71 ± 0.69 | 19.33 ± 1.39 | 1.02 ± 0.23*** | 51.92 |
|  | 50 | 6/6 | 20.39 ± 1.83 | 28.94 ± 0.87 | 0.8 ± 0.21*** | 61.11 |

*p < 0.05 compared with the model group;
**p < 0.01 compared with the model group,
***p < 0.001 compared with the model group

TABLE 21

Effect of carrimycin on the volume change of transplanted tumor of human large cell lung cancer H460 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 127.64 ± 4.93 | 2688.86 ± 53.63 | 21.07 ± 1.38 | — |
| Cyclophosphamide | 30 | 6/6 | 130.82 ± 2.38 | 1002.08 ± 48.82* | 7.66 ± 1.26* | 36.37 |
| Carrimycin | 12.5 | 6/6 | 128.59 ± 17.64 | 2000.86 ± 18.36** | 15.56 ± 0.62** | 73.83 |
|  | 25 | 6/6 | 129.58 ± 18.21 | 1688.43 ± 29.64* | 13.03 ± 0.68** | 61.83 |
|  | 50 | 6/6 | 130.02 ± 8.68 | 1365.21 ± 17.27** | 10.50 ± 0.83** | 49.82 |

*p < 0.05 compared with the model group;
**p < 0.01 compared with the model group,
***p < 0.001 compared with the model group 11. Inhibition of Carrimycin on Human Large Cell Lung Cancer in Nude Mice Model Establishment of a Mouse Solid Tumor Model H1299 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V = a \times b^2/2$; $RTV = V/V_0$ ($V_0$ is the tumor volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 22, and Table 23).

The tumor growth inhibition rates of carrimycin groups with low, medium and high doses of carrimycin are 19.57%, 49.58% and 59.65%, respectively.

The tumor volume and relative tumor volume of carrimycin groups with low, medium and high doses of carrimycin are significantly lower than those of the model group (P<0.05).

The relative tumor proliferation rates of carrimycin groups with low, medium and high doses of carrimycin are 78.57%, 63.62% and 49.71%, respectively.

There are no significant changes in the mouse weight of carrimycin groups with low, medium and high doses of carrimycin compared with the model group.

TABLE 22

Effect of carrimycin on the inhibition rate of transplanted tumor of human large cell lung cancer H1299 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 20.28 ± 1.47 | 19.25 ± 0.82 | 1.79 ± 0.29 | — |
| Cyclophosphamide | 30 | 6/6 | 20.92 ± 0.59 | 18.82 ± 0.52 | 0.56 ± 0.11*** | 68.59 |
| Carrimycin | 12.5 | 6/6 | 19.97 ± 0.82 | 18.45 ± 0.97 | 1.44 ± 0.24* | 19.57 |
|  | 25 | 6/6 | 20.48 ± 1.25 | 19.28 ± 1.16 | 0.90 ± 0.16* | 49.58 |
|  | 50 | 6/6 | 19.68 ± 1.01 | 18.82 ± 0.48 | 0.72 ± 0.13** | 59.65 |

*p < 0.05 compared with the model group;
**p < 0.01 compared with the model group,
***p < 0.001 compared with the model group

TABLE 23

Effect of carrimycin on the volume change of transplanted tumor of human large cell lung cancer H1299 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 116.72 ± 27.48 | 2273.78 ± 45.83 | 19.48 ± 0.73 | — |
| Cyclophosphamide | 30 | 6/6 | 115.38 ± 13.82 | 707.28 ± 26.96** | 6.13 ± 0.82** | 31.47 |
| Carrimycin | 12.5 | 6/6 | 116.28 ± 18.68 | 1780.25 ± 28.51* | 15.31 ± 0.49* | 78.57 |
|  | 25 | 6/6 | 117.51 ± 7.30 | 1455.95 ± 39.78** | 12.39 ± 1.85* | 63.62 |
|  | 50 | 6/6 | 115.93 ± 16.63 | 1122.20 ± 49.52** | 9.68 ± 0.51*** | 49.71 |

*p < 0.05 compared with the model group;
**p < 0.01 compared with the model group,
***p < 0.001 compared with the model group 12. Inhibition of Carrimycin on Human Renal Clear Cell Adenocarcinoma in Nude Mice Model Establishment of a Mouse Solid Tumor Model 786-O cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, and then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V = a \times b^2/2$; $RTV = V/V_0$ ($V_0$ is the tumor volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 24, and Table 25).

The tumor growth inhibition rates of carrimycin groups with low, medium and high doses of carrimycin are 30.32%, 47.24% and 63.71%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 80.81%, 67.16% and 42.82%, respectively.

There are no significant changes in the mouse weight of carrimycin groups with low, medium and high doses of carrimycin compared with the model group.

TABLE 24

Effect of carrimycin on the inhibition rate of transplanted tumor of human renal clear cell adenocarcinoma 786-O cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 22.73 ± 1.48 | 19.48 ± 0.83 | 2.18 ± 0.22 | — |
| Cyclophosphamide | 30 | 6/6 | 21.57 ± 1.31 | 20.39 ± 1.02 | 0.62 ± 0.17*** | 71.36 |
| Carrimycin | 12.5 | 6/6 | 22.08 ± 1.39 | 20.70 ± 0.49 | 1.52 ± 0.17** | 30.32 |
|  | 25 | 6/6 | 22.95 ± 1.72 | 21.26 ± 0.37 | 1.15 ± 0.19*** | 47.24 |
|  | 50 | 6/6 | 20.45 ± 0.83 | 18.59 ± 1.05 | 0.79 ± 0.17*** | 63.71 |

*p < 0.05 compared with the model group;
**p < 0.01 compared with the model group,
***p < 0.001 compared with the model group

TABLE 25

Effect of carrimycin on the volume change of transplanted tumor of human renal clear cell adenocarcinoma 786-O cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate(T/C) |
|---|---|---|---|---|---|---|
| Model Group | 0 | 6/6 | 173.29 ± 13.72 | 2901.46 ± 18.49 | 16.74 ± 1.39 | — |
| Cyclophosphamide | 30 | 6/6 | 181.48 ± 31.63 | 606.14 ± 14.34*** | 3.34 ± 0.68*** | 19.93 |
| Carrimycin | 12.5 | 6/6 | 176.32 ± 17.39 | 2385.61 ± 31.81* | 13.53 ± 1.37* | 80.81 |
|  | 25 | 6/6 | 179.63 ± 21.80 | 2019.04 ± 58.33* | 11.24 ± 0.28*** | 67.16 |
|  | 50 | 6/6 | 180.36 ± 14.79 | 1293.18 ± 19.84** | 7.17 ± 1.82*** | 42.82 |

*p < 0.05 compared with the model group;
**p < 0.01 compared with the model group,
***p < 0.001 compared with the model group 13. Inhibition of Carrimycin on Human Renal Cell Adenocarcinoma in Nude Mice Model Establishment of a Mouse Solid Tumor Model 769-P cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1\times10^7$/ml with matrigel, and then each nude mouse was inoculated subcutaneously with 0.2 ml of cells at its right armpit and recorded as the first day of inoculation. When the tumor growed to be greater than or equal to 100 mm$^3$, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V = a \times b^2/2$; $RTV = V/V_0$ ($V_0$ is the tumor volume before administration, V is the tumor volume before sacrifice), and T/C (%) = treatment group RTV/model control group RTV × 100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%) = (1−the average tumor weight of the treatment group/the average tumor weight of the model group) × 100%.

The test results show that compared with the control group, each drug-administered group has a certain degree of inhibition on the tumor growth inhibition rate, tumor volume, relative tumor volume and relative tumor proliferation rate (see Table 26, and Table 27).

The tumor growth inhibition rates of carrimycin groups with low, medium and high doses of carrimycin are 38.40%, 53.67% and 69.53%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 62.29%, 43.16% and 31.34%, respectively.

There are no significant changes in the mouse weight of carrimycin groups with low, medium and high doses of carrimycin compared with the model group.

every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V=a \times b^2/2$; $RTV=V/V_0$ ($V_0$ is the tumor

TABLE 26

Effect of carrimycin on the inhibition rate of transplanted tumor of human renal cell adenocarcinoma 769-P cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 22.29 ± 1.40 | 20.78 ± 0.23 | 2.57 ± 0.16 | — |
| Cyclophosphamide | 30 | 6/6 | 22.48 ± 0.91 | 21.28 ± 0.39 | 0.61 ± 0.15*** | 76.09 |
| Carrimycin | 12.5 | 6/6 | 21.82 ± 1.19 | 20.19 ± 1.82 | 1.58 ± 0.30** | 38.40 |
| | 25 | 6/6 | 22.14 ± 0.38 | 20.85 ± 1.03 | 1.19 ± 0.33*** | 53.67 |
| | 50 | 6/6 | 21.95 ± 0.79 | 20.36 ± 1.05 | 0.78 ± 0.20*** | 69.53 |

*p < 0.05 compared with the model group;
**p < 0.01 compared with the model group,
***p < 0.001 compared with the model group

TABLE 27

Effect of carrimycin on the volume change of transplanted tumor of human renal cell adenocarcinoma 769-P cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate (T/C) |
|---|---|---|---|---|---|---|
| Model Group | 0 | 6/6 | 179.55 ± 29.72 | 3820.824 ± 231.47 | 21.28 ± 1.37 | — |
| Cyclophosphamide | 30 | 6/6 | 178.48 ± 28.78 | 747.83 ± 138.57*** | 4.19 ± 1.29** | 19.68 |
| Carrimycin | 12.5 | 6/6 | 180.23 ± 27.35 | 2389.85 ± 184.29** | 13.26 ± 1.05* | 62.29 |
| | 25 | 6/6 | 179.84 ± 45.71 | 1650.93 ± 101.45** | 9.18 ± 0.71*** | 43.16 |
| | 50 | 6/6 | 178.92 ± 37.28 | 1193.40 ± 124.76*** | 6.67 ± 1.28*** | 31.34 |

*p < 0.05 compared with the model group;
**p < 0.01 compared with the model group,
***p < 0.001 compared with the model group 14. Inhibition of Carrimycin on Human Glioma in Nude Mice Model Establishment of a Mouse Solid Tumor Model U251 cells in a logarithmic growth phase were taken and subjected to a trypan blue exclusion experiment showing that the cell viability was more than 95%, then the cells were subject to trypsinization, centrifugation, and supernatant removal. Then matrigel cell concentration was adjusted to $1 \times 10^7$/ml with matrigel, and then each nude mouse was inoculated subcutaneously with 0.2 ml of cells at its right armpit and recorded as the first day of inoculation. When the tumor growed to be greater than or equal to 100 mm$^3$, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of tumor, and the body weight of each mouse were recorded volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 28, and Table 29).

The tumor growth inhibition rates of carrimycin groups with low, medium and high doses of carrimycin are 66.51%, 79.59% and 81.82%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 84.81%, 56.30% and 35.90%, respectively.

There are no significant changes in the mouse weight of carrimycin groups with low, medium and high doses of carrimycin compared with the model group.

the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following

TABLE 28

Effect of carrimycin on the inhibition rate of transplanted tumor of human glioma U251 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 23.53 ± 2.24 | 20.70 ± 1.73 | 2.09 ± 0.13 | — |
| Cyclophosphamide | 30 | 6/6 | 22.24 ± 1.53 | 19.92 ± 1.68 | 0.42 ± 0.10*** | 79.74 |
| Carrimycin | 12.5 | 6/6 | 22.46 ± 3.64 | 19.72 ± 1.57 | 0.70 ± 0.18* | 66.51 |
| | 25 | 6/6 | 21.21 ± 2.16 | 19.97 ± 1.81 | 0.43 ± 0.03** | 79.59 |
| | 50 | 6/6 | 21.86 ± 1.68 | 19.99 ± 1.70 | 0.38 ± 0.03*** | 81.82 |

*$p < 0.05$ compared with the model group;
**$p < 0.01$ compared with the model group,
***$p < 0.001$ compared with the model group

TABLE 29

Effect of carrimycin on the volume change of transplanted tumor of human glioma U251 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate (T/C) |
|---|---|---|---|---|---|---|
| Model Group | 0 | 6/6 | 102.63 ± 12.94 | 1002.83 ± 77.59 | 9.77 ± 2.75 | — |
| Cyclophosphamide | 30 | 6/6 | 98.40 ± 25.25 | 566.33 ± 39.32*** | 5.75 ± 1.22** | 56.84 |
| Carrimycin | 12.5 | 6/6 | 98.97 ± 15.26 | 846.82 ± 39.34 | 0.59 ± 2.81 | 84.81 |
| | 25 | 6/6 | 99.68 ± 16.45 | 563.07 ± 49.17** | 5.67 ± 3.12** | 56.30 |
| | 50 | 6/6 | 102.75 ± 24.04 | 360.75 ± 44.98** | 3.52 ± 1.51** | 35.90 |

*$p < 0.05$ with the model group;
**$p < 0.01$ compared with the model group,
***$p < 0.001$ compared with the model group 15. Inhibition of Carrimycin on Human Glioblastoma in Nude Mice Model Establishment of a Mouse Solid Tumor Model A172 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1\times10^7$/ml with matrigel, then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of formulas, wherein $V=a\times b^2/2$; $RTV=V/V_0$ ($V_0$ is the tumor volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 30, and Table 31).

The tumor growth inhibition rates of carrimycin groups with low, medium and high doses of carrimycin are 46.95%, 66.84% and 76.26%, respectively.

The tumor volume and relative tumor volume of carrimycin groups with low, medium and high doses of carrimycin are significantly lower than those of the model group (P<0.05).

The relative tumor proliferation rates of carrimycin groups with low, medium and high doses of carrimycin are 68.62%, 55.91% and 38.53%, respectively.

There are no significant changes in the mouse weight of carrimycin groups with low, medium and high doses of carrimycin compared with the model group.

TABLE 30

Effect of carrimycin on the inhibition rate of transplanted tumor of human glioblastoma A172 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 22.21 ± 1.34 | 20.57 ± 1.71 | 2.72 ± 0.25 | — |
| Cyclo-phosphamide | 30 | 6/6 | 22.89 ± 1.22 | 19.27 ± 1.49 | 0.85 ± 0.18** | 68.68 |
| Carrimycin | 12.5 | 6/6 | 21.54 ± 1.27 | 18.20 ± 1.33 | 1.45 ± 0.29* | 46.95 |
|  | 25 | 6/6 | 21.88 ± 1.46 | 18.56 ± 1.67 | 0.90 ± 0.31** | 66.84 |
|  | 50 | 6/6 | 21.36 ± 1.82 | 18.47 ± 1.98 | 0.65 ± 0.10** | 76.26 |

*p < 0.05 compared with the model group,
**p < 0.01 compared with the model group,
***p < 0.001 compared with the model group

TABLE 31

Effect of carrimycin on the volume change of transplanted tumor of human glioblastoma A172 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate (T/C) |
|---|---|---|---|---|---|---|
| Model Group | 0 | 6/6 | 128.06 ± 6.31 | 1931.35 ± 95.62 | 15.10 ± 2.721 | — |
| Cyclo-phosphamide | 30 | 6/6 | 122.41 ± 14.06 | 1430.80 ± 134.31*** | 11.78 ± 3.25*** | 75.42 |
| Carrimycin | 12.5 | 6/6 | 121.32 ± 8.54 | 1303.03 ± 175.53* | 10.79 ± 3.21* | 68.62 |
|  | 25 | 6/6 | 111.32 ± 7.45 | 1060.58 ± 134.52*** | 9.54 ± 2.41*** | 55.91 |
|  | 50 | 6/6 | 128.93 ± 2.60 | 731.34 ± 130.20*** | 5.67 ± 2.25*** | 38.53 |

*p < 0.05 compared with the model group;
**p < 0.001 compared with the model group,
***p < 0.001 compared with the model group 16. Inhibition of Carrimycin on Human Pancreatic Cancer in Nude Mice Model Establishment of a Mouse Solid Tumor Model PANC-1 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, and then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following formulas, wherein $V = a \times b^2/2$; $RTV = V/V_0$ ($V_0$ is the tumor volume before administration, V is the tumor volume before sacrifice), and T/C (%)=treatment group RTV/model control group RTV×100%

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 32, and Table 33).

The tumor growth inhibition rates of carrimycin groups with low, medium and high doses of carrimycin are 56.27%, 62.66% and 75.94%, respectively.

The tumor volume and relative tumor volume of carrimycin groups with low, medium and high doses of carrimycin are significantly lower than those of the model group (P<0.05).

The relative tumor proliferation rates of carrimycin groups with low, medium and high doses of carrimycin are 74.10%, 47.01% and 35.55%, respectively.

There are no significant changes in the mouse weight of carrimycin groups with low, medium and high doses of carrimycin compared with the model group.

were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate

TABLE 32

Effect of carrimycin on the inhibition rate of transplanted tumor of human pancreatic cancer PANC-1 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 22.21 ± 1.07 | 20.32 ± 1.88 | 3.74 ± 0.33 | — |
| Cyclophosphamide | 30 | 6/6 | 21.89 ± 1.88 | 19.92 ± 1.68 | 0.73 ± 0.09** | 80.43 |
| Carrimycin | 12.5 | 6/6 | 21.71 ± 1.94 | 19.42 ± 1.37 | 1.64 ± 0.21* | 56.27 |
|  | 25 | 6/6 | 21.68 ± 1.25 | 19.97 ± 1.01 | 1.40 ± 0.06** | 62.66 |
|  | 50 | 6/6 | 21.99 ± 1.40 | 19.36 ± 1.73 | 0.90 ± 0.18*** | 75.94 |

*p < 0.05 compared with the model group,
**p < 0.01 compared with the model group,
***p < 0.001 compared with the model group

TABLE 33

Effect of carrimycin on the volume change of transplanted tumor of human pancreatic cancer PANC-1 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate (T/C) |
|---|---|---|---|---|---|---|
| Model Group | 0 | 6/6 | 95.97 ± 7.55 | 944.72 ± 20.38 | 9.89 ± 0.91 | — |
| Cyclophosphamide | 30 | 6/6 | 93.73 ± 8.27 | 515.49 ± 32.36*** | 5.54 ± 0.72** | 54.55 |
| Carrimycin | 12.5 | 6/6 | 92.14 ± 6.55 | 700.24 ± 46.53** | 4.66 ± 0.69 | 74.10 |
|  | 25 | 6/6 | 95.65 ± 6.65 | 443.69 ± 21.37*** | 4.66 ± 0.44** | 47.01 |
|  | 50 | 6/6 | 94.97 ± 7.60 | 335.43 ± 29.30*** | 3.54 ± 0.26** | 35.55 |

*p < 0.05 compared with the model group;
**p < 0.01 compared with the model group,
***p < 0.001 compared with the model group 17. Inhibition of Carrimycin on Human Esophageal Cancer in Nude Mice Model Establishment of a Mouse Solid Tumor Model TE-1 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to $1 \times 10^7$/ml with matrigel, and then each nude mouse was inoculated subcutaneously with 0.2 ml of cells at its right armpit and recorded as the first day of inoculation. When the tumor growed to be greater than or equal to 100 mm³, the mice (T/C) are calculated respectively according to the following formulas, wherein $V = a \times b^2/2$; $RTV = V/V_0$ ($V_0$ is the tumor volume before administration, V is the tumor volume before sacrifice), and T/C (%) = treatment group RTV/model control group RTV × 100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the model group, each drug-administered group has a certain degree of inhibition on the tumor growth inhibition rate, tumor volume, relative tumor volume and relative tumor proliferation rate (see Table 34, and Table 35).

The tumor growth inhibition rates of carrimycin groups with low, medium and high doses of carrimycin are 46.71%, 61.48% and 70.41%, respectively.

The tumor volume and relative tumor volume of carrimycin groups with low, medium and high doses of carrimycin are significantly lower than those of the model group ($P<0.05$).

The relative tumor proliferation rates of carrimycin groups with low, medium and high doses of carrimycin are 64.79%, 46.03% and 37.02%, respectively.

There are no significant changes in the mouse weight of carrimycin groups with low, medium and high doses of carrimycin compared with the model group.

$1\times10^7$/ml with matrigel, and then each nude mouse was inoculated subcutaneously with 0.2 ml of cells at its right armpit and recorded as the first day of inoculation. When the tumor growed to be greater than or equal to 100 mm³, the mice were randomly divided into 5 groups with 6 mice in each group: a model group, a cyclophosphamide group, and carrimycin groups with doses of 12.5, 25 and 50 mg/kg. Each group was continuously administered intragastrically for 30 days with a dose of 20 ml/kg. The mice were sacrificed the next day after drug withdrawal and the indicators were tested. The long diameter and short diameter of the tumor, and the body weight of each mouse were recorded every 3 days from drug administration to nude mouse sacrifice.

Calculation of Tumor Volume and Relative Tumor Proliferation Rate

The body weight of the nude mice and the long diameter (a) and short diameter (b) of the transplanted tumor were measured every 3 days, and the tumor volume (v), relative tumor volume (RTV) and relative tumor proliferation rate (T/C) are calculated respectively according to the following

TABLE 34

Effect of carrimycin on the inhibition rate of transplanted tumor of human esophageal cancer TE-1 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 23.21 ± 0.93 | 20.95 ± 1.27 | 2.36 ± 0.37 | — |
| Cyclophosphamide | 30 | 6/6 | 22.78 ± 1.35 | 21.32 ± 1.63 | 0.66 ± 0.28*** | 72.12 |
| Carrimycin | 12.5 | 6/6 | 22.63 ± 1.35 | 20.33 ± 1.83 | 1.26 ± 0.16* | 46.71 |
| | 25 | 6/6 | 22.38 ± 1.35 | 20.93 ± 1.77 | 0.91 ± 0.26** | 61.48 |
| | 50 | 6/6 | 22.80 ± 2.52 | 20.75 ± 1.92 | 0.70 ± 0.22** | 70.41 |

*$p < 0.05$ compared with the model group,
**$p < 0.01$ compared with the model group,
***$p < 0.001$ compared with the model group

TABLE 35

Effect of carrimycin on the volume change of transplanted tumor of human esophageal cancer TE-1 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate (T/C) |
|---|---|---|---|---|---|---|
| Model Group | 0 | 6/6 | 92.60 ± 14.32 | 1598.02 ± 58.89 | 17.28 ± 1.03 | — |
| Cyclophosphamide | 30 | 6/6 | 92.02 ± 7.06 | 830.30 ± 34.31*** | 9.05 ± 2.58*** | 52.01 |
| Carrimycin | 12.5 | 6/6 | 96.13 ± 14.13 | 1036.36 ± 87.06* | 10.82 ± 2.31* | 64.79 |
| | 25 | 6/6 | 100.21 ± 9.72 | 734.98 ± 11.18** | 7.39 ± 1.35*** | 46.03 |
| | 50 | 6/6 | 98.80 ± 10.03 | 591.34 ± 61.75*** | 6.01 ± 1.87*** | 37.02 |

*$p < 0.05$ compared with the model group;
**$p < 0.01$ compared with the model group,
***$p < 0.001$ with the model group 18. Inhibition of Carrimycin on Human Gastric Adenocarcinoma in Nude Mice Model Establishment of a Mouse Solid Tumor Model SGC7901 cells in a logarithmic growth phase were taken and subjected to a trypan blue exclusion experiment showing that the cell viability was more than 95%, then the cells were subjected to trypsinization, centrifugation, and supernatant removal. Then cell concentration was adjusted to formulas, wherein $V=a\times b^2/2$; $RTV=V/V_0$ ($V_0$ is the tumor volume before administration, V is the tumor volume before sacrifice), and T/C (%)=treatment group RTV/model control group RTV×100%.

Calculation of Tumor Growth Inhibition Rate

Each mouse was weighed and sacrificed. After the tumor was completely stripped off from the body of the mouse, the non-tumor tissues such as blood stains and fat were removed to weigh the tumor and calculate the tumor growth inhibition rate. The average tumor weight of each group of mice is used as an indicator of efficacy. Tumor growth inhibition rate (%)=(1−the average tumor weight of the treatment group/the average tumor weight of the model group)×100%.

The test results show that compared with the control group, each drug-administered group has a certain degree of inhibition on the tumor growth inhibition rate, tumor volume, relative tumor volume and relative tumor proliferation rate (see Table 36, and Table 37).

The tumor growth inhibition rates of carrimycin groups with low, medium and high doses of carrimycin are 42.51%, 68.92% and 74.49%, respectively.

The tumor volume and relative tumor volume of carrimycin groups with low, medium and high doses of carrimycin are significantly lower than those of the model group (P<0.05).

The relative tumor proliferation rates of carrimycin groups with low, medium and high doses of carrimycin are 69.12%, 47.88% and 38.35%, respectively.

There are no significant changes in the mouse weight of carrimycin groups with low, medium and high doses of carrimycin compared with the model group.

19. Inhibition of Transplanted Tumors of Mouse $H_{22}$ Liver Cancer and Mouse Lewis Lung Cancer Establishment of a Mouse Solid Tumor Model:

The $H_{22}$ cell strains cryopreserved in liquid nitrogen were resuscitated in Kunming mice. After 3 generations, the ascites of Kunming mice were taken and placed in a 50 ml centrifuge tube in which 10 ml of 0.9% normal saline was added, and then centrifuging was performed at 1000 rpm for 5 min at room temperature, and the obtained supernatant was removed. Then 10 ml of 0.9% normal saline was added to the tube to blow and mix well, and then the mixture was diluted to $5\times10^6$ live cells/ml with normal saline after counting. The tube was stored in ice water, and 75% ethanol was used to disinfect the skin under the right armpits of the mice. Each Kunming mouse was soon inoculated subcutaneously with 0.2 ml of the cells at the armpit of the right forelimb.

Lewis lung cancer cells were cultured in a RPMI 1640 culture medium containing 10% fetal bovine serum at 37° C. in a 5% $CO_2$ incubator. The cells in the logarithmic growth phase were subjected to trypsinization with 0.25% trypsin, then the cells were collected to be centrifugated to remove the obtained supernatant, then were washed twice with

TABLE 36

Effect of carrimycin on the inhibition rate of transplanted tumor of human gastric adenocarcinoma SGC7901 cells in nude mice ($\bar{x} \pm s$)

| Group | Dose (mg/kg) | Number of Animals (Start/End) | Body Weight (g)(d1) | Body Weight (g)(d30) | Tumor Weight (g) | Inhibition Rate (%) |
|---|---|---|---|---|---|---|
| Model Group | 0 | 6/6 | 22.24 ± 1.75 | 19.90 ± 1.73 | 2.43 ± 0.29 | — |
| Cyclophosphamide | 30 | 6/6 | 21.80 ± 1.96 | 20.25 ± 1.57 | 0.71 ± 0.08** | 70.97 |
| Carrimycin | 12.5 | 6/6 | 21.05 ± 1.53 | 19.22 ± 1.37 | 1.40 ± 0.27* | 42.51 |
|  | 25 | 6/6 | 21.75 ± 1.67 | 19.25 ± 1.54 | 0.76 ± 0.10** | 68.92 |
|  | 50 | 6/6 | 21.83 ± 1.34 | 19.59 ± 4.26 | 0.60 ± 0.14** | 74.49 |

*p < 0.05 compared with the model group;
**p < 0.01 compared with the model group,
***p < 0.001 with the model group

TABLE 37

Effect of carrimycin on the volume change of transplanted tumor of human gastric adenocarcinoma SGC7901 cells in nude mice ($\bar{x} \pm s$)

| Group | Dose (mg/kg) | Number of Animals (Start/End) | Tumor Volume (mm3) (d1) | Tumor Volume (mm3) (d30) | Relative Tumor Volume (RTV) | Relative Tumor Proliferation Rate (T/C) |
|---|---|---|---|---|---|---|
| Model Group | 0 | 6/6 | 119.15 ± 8.54 | 1638.68 ± 139.34 | 13.78 ± 3.16 | — |
| Cyclophosphamide | 30 | 6/6 | 102.45 ± 9.52 | 799.74 ± 82.25** | 7.86 ± 3.23** | 48.83 |
| Carrimycin | 12.5 | 6/6 | 109.74 ± 12.891 | 1123.03 ± 78.59* | 10.30 ± 2.99* | 69.12 |
|  | 25 | 6/6 | 118.90 ± 12.69 | 781.65 ± 31.55** | 6.64 ± 2.97** | 47.88 |
|  | 50 | 6/6 | 121.21 ± 7.73 | 622.34 ± 58.74** | 5.41 ± 2.66** | 38.35 |

*p < 0.05 compared with the model group;
**p < 0.01 compared with the model group,
***p < 0.001 compared with the model group sterile normal saline. And then the cells were suspended in the normal saline to be subjected to a trypan blue staining assay which shows that the cell viability was greater than 95%, and then cell counting was performed. The Lewis cells were adjusted to $1 \times 10^7$/mL in concentration and stored in ice water. 75% ethanol was used to disinfect the skin under the right armpits of the mice, and each C57BL/6 mouse was soon inoculated subcutaneously with 0.2 ml of the cells at its right armpit.

Mouse Grouping and Administration Method

In the $H_{22}$ liver cancer model, the mice inoculated with the tumor were randomly divided into groups with 10 mice in each group on the next day of inoculation. The groups included: a model control group, a positive drug cyclophosphamide control group (CTX, 26 mg/kg), and three carrimycin groups with doses of 13, 26 and 53 mg/kg. Each group was continuously administered intragastrically for 7 days with a dose of 20 ml/kg.

In the Lewis lung cancer model, the mice inoculated with the tumor were randomly divided into groups with 10 mice in each group on the next day of inoculation. The groups included: a model control group, a positive drug cyclophosphamide control group (CTX, 30 mg/kg), and three carrimycin groups with doses of 13, 26 and 52 mg/kg. Each group was continuously administered intragastrically for 15 days with a dose of 20 ml/kg.

Calculation of the Tumor Inhibition Rate:

The tumor-bearing mice were weighed and sacrificed the next day after the last administration. The subcutaneous tumors were dissected and weighed. The average tumor weight of each group is calculated, and the tumor inhibition rate is calculated.

Tumor inhibition rate=$(1-T/C) \times 100\%$

T: average tumor weight of the drug-administered group;
C: average tumor weight of the blank control group.

Results:

1. Inhibition of Carrimycin on the Transplanted Tumor of Mouse $H_{22}$ Liver Cancer As can be seen from the results of Table 38, the tumor inhibition rate of the positive drug cyclophosphamide control group to Kunming mouse $H_{22}$ liver cancer is 47.25%. Carrimycin groups with doses of 26 and 52 mg/kg significantly inhibit the growth of $H_{22}$ liver cancer in mice with the tumor inhibition rates of 50.67% and 79.50%, respectively. The tumor inhibition rate of the carrimycin group with a dose of 52 mg/kg is significantly lower than that of the positive control group ($P<0.05$).

The positive drug cyclophosphamide group shows a slight decrease in weight compared with the normal control group. The weight of the mice in each of the carrimycin groups increases compared with that before the administration, but there is no significant difference compared with the model control group.

TABLE 38

Inhibition of carrimycin on the transplanted tumor of mouse $H_{22}$ liver cancer ($\bar{x} \pm s$)

| Group | Dose (mg/kg) | Number of Animals (Start/End) | Body Weight (g)(d1) | Body Weight (g) (d7) | tumour (g) | Inhibition Rate (%) |
|---|---|---|---|---|---|---|
| Model Group | 0 | 10/10 | 24.17 ± 1.31 | 29.85 ± 1.76 | 1.00 ± 0.13 | |
| Cyclophosphamide | 26 | 10/10 | 23.50 ± 1.90 | 25.13 ± 2.69** | 0.53 ± 0.24* | 47.25 |
| Carrimycin | 13 | 10/10 | 23.21 ± 1.19 | 29.30 ± 1.45 | 0.74 ± 0.11** | 25.85 |
| | 26 | 10/10 | 23.68 ± 1.01 | 28.73 ± 1.69 | 0.49 ± 0.18** | 50.67 |
| | 52 | 10/10 | 24.20 ± 1.26 | 28.95 ± 1.28 | 0.20 ± 0.07**## | 79.50 |

*p < 0.05 compared with the model group;
**p < 0.01 compared with the model group;
p < 0.05 compared with the cyclophosphamide group 2. Inhibition of Carrimycin on the Transplanted Tumor of Mouse Lewis Lung Cancer As can be seen from the results of Table 39, the tumor inhibition rate of the positive drug cyclophosphamide control group to mouse Lewis lung cancer is 49.14%. Carrimycin groups with doses of 13, 26 and 52 mg/kg significantly inhibit the growth of mouse Lewis lung cancer in mice with the tumor inhibition rates of 50.30%, 55.88% and 76.23%, respectively. The tumor inhibition rate of the carrimycin group with a dose of 52 mg/kg is significantly lower than that of the positive control group ($P<0.05$). The weight of the mice in each of the carrimycin groups increases compared with that before the administration, but there is no significant difference compared with the model control group.

TABLE 39

Inhibition of carrimycin on the transplanted tumor of mouse Lewis lung cancer ($\bar{x} \pm s$)

| Group | Dose (mg/kg) | Number of Animals (Start/End) | Body Weight (g) (d1) | Body Weight (g) (d15) | Tumor Weight (g) | Inhibition Rate (%) |
|---|---|---|---|---|---|---|
| Model Group | 0 | 10/10 | 22.35 ± 1.44 | 23.94 ± 1.17 | 1.16 ± 0.39 | |
| Cyclophosphamide | 26 | 10/10 | 25.60 ± 2.06 | 20.14 ± 3.26 | 0.59 ± 0.13** | 49.14 |

TABLE 39-continued

Inhibition of carrimycin on the transplanted tumor of mouse Lewis lung cancer ($\bar{x} \pm s$)

| Group | Dose (mg/kg) | Number of Animals (Start/End) | Body Weight (g) (d1) | Body Weight (g) (d15) | Tumor Weight (g) | Inhibition Rate (%) |
|---|---|---|---|---|---|---|
| Carrimycin | 13 | 10/10 | 21.83 ± 1.24 | 22.42 ± 0.94 | 0.58 ± 0.38** | 50.30 |
|  | 26 | 10/10 | 22.39 ± 1.45 | 22.43 ± 0.98 | 0.51 ± 0.23* | 55.88 |
|  | 52 | 10/10 | 21.69 ± 1.67 | 21.76 ± 0.84 | 0.28 ± 0.18** | 76.23 |

*p < 0.05 compared with the model group;
**p < 0.01 compared with the model group;
p < 0.05 compared with the cyclophosphamide group 20. Effect of Carrimycin on Immune Function of Tumor-Bearing Mice Method 1. Effect on Thymus Index and Spleen Index of Tumor-Bearing Mice After the tumor-bearing mice are sacrificed, the spleen and thymus are weighed, and the spleen index and thymus index are calculated.

2. Effects on Lymphocyte Proliferation Activity and Natural Killer (NK) Cell Activity of Tumor-Bearing Mice 2.1 Preparation of Spleen Lymphocytes The serum-free RPMI 1640 medium was placed in a dish, and then the dish was placed on ice. The spleen was aseptically taken and gently ground with a sterile glass slide to prepare a single cell suspension. The single cell suspension was filtered with a double-layer sterile gauze, washed twice with serum-free RPMI 1640 medium, and centrifuged at 1,500 rpm for 5 min to remove the obtained supernatant. 2 mL of red blood cell lysate was added to the treated suspension, the mixture was allowed to stand for 2 min, and then 8 mL of RPMI 1640 medium was added, centrifuging was performed at 1,500 rpm for 5 min to remove the obtained supernatant, and then washing was performed twice with the RPMI 1640 medium. Trypan blue staining was performed to count the number of live cells, and the cell viability was more than 95%. A single cell suspension was prepared by using a RPMI 1640 medium containing 10% fetal bovine serum.

2.2 Spleen Lymphocyte Proliferation Activity Assay

The spleen cell suspension was taken, and the cell density was adjusted to $1\times10^7$/mL. Each mouse was set with: A. a control well: 100 μL of RPMI 1640 medium was added; B. a concanavalin A (ConA) stimulation well: 100 μL (10 mg/L) of concanavalin A (ConA) solution was added; and C. a bacterial endotoxin (LPS) stimulating well: 100 μL (20 mg/L) of bacterial endotoxin (LPS) solution was added. The above cells were added to a 96-well plate, and then 100 μL of spleen cell suspension was added to each of the above wells. After the culture plate was transferred to a saturated humidity condition with a volume fraction of 5% $CO_2$ at 37° C. for incubation for 72 h, 10 μL of MTT solution (5 g/L) was added to each well, and incubation was continued to be performed for 4 hours under the same conditions, then the culture was terminated. 100 μl of a triple solution (SDS 10 g, 10M HCl 0.1 mL, isobutanol 5 mL, diluted with distilled water to 100 mL) was added, and the plate was shaken for 10 min to fully dissolve the crystals. The Optical Density (OD) of each well was measured at 570 nm, and the lymphocyte proliferation rate was calculated. Lymphocyte proliferation rate (%)=[(T−C)/C]×100%, wherein T is the Optical Density of the stimulation well, and C is the Optical Density of the control well.

2.3 Natural Killer (NK) Cell Activity Assay

The spleen cell suspension was taken, and the cell density was adjusted to $1\times10^7$/mL (effector cells). A suspension of K562 cells was prepared with a cell density of $1\times10^5$/mL (target cells). Each mouse was set with: A. effector cells: target cell well (quantity ratio 20:1) to which 20 μL of spleen cell suspension and 100 μL of K562 cell suspension were added; B. an effector cell control well, to which 100 μL of spleen cell suspension and 100 μL of RPMI 1640 medium were added; and C. a target cell control well, to which 100 μL of K562 cell suspension and 100 μL of RPMI 1640 medium were added. The above cells were added to the 96-well plate. After the 96-well plate was transferred to a saturated humidity condition with a volume fraction of 5% $CO_2$ at 37° C. for incubation for 22 h, 10 μL of MTT solution (5 g/L) was added to each well, and incubation was continued to be performed for 4 hours under the same conditions, then the culture was terminated. 100 μl of a triple solution (SDS 10 g, 10M HCl 0.1 mL, isobutanol 5 mL, diluted with distilled water to 100 mL) was added, and the plate was shaken for 10 min to fully dissolve the crystals, and the Optical Density (OD) of each well at 490 nm was measured, and the NK cell activity was calculated. NK cell activity (%)=[TO−(S−E)]/TO×100%, wherein TO is the Optical Density of the target cell control well, S is the Optical Density of the effector cell control well, and E is the Optical Density of the effector cell.

Results:

1. Effect on Thymus Index and Spleen Index of $H_{22}$ Liver Cancer Tumor-Bearing Mice As can be seen from the results of Table 40, the thymus index and spleen index of the positive drug cyclophosphamide control group are significantly lower than those of the control group (P<0.01). The thymus indexes of the mice in the carrimycin groups with doses of 13, 26 and 52 mg/kg have no significant change compared with that of the control group. The spleen index of the carrimycin group with a dose of 52 mg/kg significantly increases compared with that of the control group (P<0.05).

TABLE 40

Effect of carrimycin on thymus index and spleen index (w) of $H_{22}$ liver tumor-bearing mice ($\bar{x} \pm s$)

| Group | Dose (mg/kg) | Spleen Index (%) | Thymus Index (%) |
|---|---|---|---|
| Control Group | 0 | 0.66 ± 0.12 | 0.13 ± 0.05 |
| Cyclophosphamide | 26 | 0.38 ± 0.09** | 0.04 ± 0.02** |
| Carrimycin | 13 | 0.72 ± 0.07 | 0.15 ± 0.07 |
|  | 26 | 0.60 ± 0.15 | 0.14 ± 0.01 |
|  | 52 | 0.86 ± 0.25* | 0.12 ± 0.04 |

**p < 0.01 compared with the control group

2. Effect on Thymus Index and Spleen Index of Lewis Lung Cancer Tumor-Bearing Mice As can be seen from the results in Table 41, the spleen index of the positive drug cyclophosphamide control group is significantly lower than that of the control group (P<0.01). The spleen index and thymus index of the mice in the carrimycin groups with doses of 13, 26 and 52 mg/kg are not significantly different from those in the control group.

TABLE 41

Effect of carrimycin on thymus index and spleen index (w) in Lewis lung cancer-bearing mice ($\bar{x} \pm s$, n = 6)

| Group | Dose (mg/kg) | Spleen Index (%) | Thymus Index (%) |
|---|---|---|---|
| Control Group | 0 | 0.96 ± 0.49 | 0.12 ± 0.03 |
| Cyclophosphamide | 26 | 0.41 ± 0.12** | 0.12 ± 0.09 |
| Carrimycin | 13 | 0.98 ± 0.37 | 0.11 ± 0.03 |
|  | 26 | 1.33 ± 0.49 | 0.10 ± 0.05 |
|  | 52 | 1.09 ± 0.17 | 0.09 ± 0.02 |

**$p < 0.01$ compared with the control group;
*$p < 0.05$ compared with the control group;

3. Effect on NK Cell Activity of Lewis Lung Cancer Tumor-Bearing Mice

As can be seen from the results in Table 42, the NK cell activity of the positive drug cyclophosphamide control group is significantly lower than that of the control group (P<0.05). The NK cell activities of the carrimycin groups with doses of 13 and 26 mg/kg significantly increase compared with that of the control group (P<0.01).

TABLE 42

Effect of carrimycin on the NK cell activity of Lewis lung cancer tumor-bearing ($\bar{x} \pm s$, n = 6)

| Group | Dose(mg/kg) | NK Cell Activity (%) |
|---|---|---|
| Control Group | 0 | 35.2 ± 7.2 |
| Cyclophosphamide | 26 | 25.4 ± 6.6* |
| Carrimycin | 13 | 52.5 ± 9.2** |
|  | 26 | 67.0 ± 12.1** |
|  | 52 | 39.8 ± 6.8 |

**$p < 0.01$ compared with the control group;
*$p < 0.05$ compared with the control group;

4. Effect on Lymphocyte Proliferation Activity of Lewis Lung Cancer Tumor-Bearing Mice As can be seen from the results in Table 43, the lymphocyte activity of the positive drug cyclophosphamide control group is significantly inhibited (P<0.05). The lymphocyte activities of the carrimycin groups with doses of 13 and 26 mg/kg significantly increase compared with that of the control group (P<0.05, P<0.01).

TABLE 43

Effect of carrimycin on lymphocyte proliferation in transplanted tumor of Lewis lung cancer mice ($\bar{x} \pm s$, n = 6)

| Group | Dose (mg/kg) | B Lymphocyte Proliferation Activity (%) | T Lymphocyte Proliferation Activity (%) |
|---|---|---|---|
| Control Group | 0 | 30.37 ± 10.16 | 17.60 ± 7.39 |
| Cyclophosphamide | 26 | 11.63 ± 4.68* | 13.24 ± 3.72* |
| Carrimycin | 13 | 41.63 ± 7.06* | 25.27 ± 8.2** |
|  | 26 | 44.81 ± 4.41* | 36.24 ± 2.15** |
|  | 52 | 32.71 ± 1.84 | 22.26 ± 4.33 |

*$p < 0.05$ compared with the control group;
**$p < 0.01$ compared with the control group;

5. Effect on Spleen Index of A549 Lung Cancer Tumor-Bearing Mice

As can be seen from the results in Table 44, the spleen index of the positive drug cyclophosphamide control group is significantly lower than that of the control group (P<0.01). The spleen indexes of the mice in the carrimycin groups with doses of 13, 26 and 52 mg/kg do not change significantly compared with that of the control group.

TABLE 44

Effect of carrimycin on spleen index of A549 lung cancer tumor-bearing mice ($\bar{x} \pm s$, n = 6)

| Group | Dose (mg/kg) | Spleen Index (%) |
|---|---|---|
| Control Group | 0 | 0.31 ± 0.04 |
| Cyclophosphamide | 26 | 0.20 ± 0.03** |
| Carrimycin | 13 | 0.32 ± 0.05 |
|  | 26 | 0.38 ± 0.15 |
|  | 52 | 0.31 ± 0.06 |

**$p < 0.01$ compared with the control group

Test Example 3 Clinical Trial

The present disclosure collects a plurality of clinical cases, wherein some patient had breast cancer, suffering from severe pain symptoms. After the patient took the carrimycin tablets (prepared in Embodiment 1) for 2 courses (30 days for 1 course, administered orally, 2 tablets per day), the attending physician diagnosed the tumor to be smaller. The patient herself also felt pain relief and had better mental condition.

Some patient had renal clear cell adenocarcinoma, and the imaging examination diagnosed the shadow of the kidney with renal tumors accounted for two-thirds of the left kidney area. And the pathological result was early-stage renal clear cell adenocarcinoma. After the patient took the carrimycin tablets (prepared in Embodiment 1) for 2 courses (30 days for 1 course, administered orally, 2 tablets per day), the attending physician diagnosed that the tumor area of the kidney was reduced and improved significantly.

Some patient had gliomas and was diagnosed with brain tissue infiltration and destruction, and peripheral cerebral edema was also significant. And the patient also suffered from symptoms such as headache and vision loss. After the patient took the carrimycin tablets (prepared in Embodiment 1) for 2 courses (30 days for 1 course, administered orally, 2 tablets per day), the attending physician diagnosed that the edema was relieved, and the patient felt the symptoms were relieved and improved significantly.

Some patient had lymphoma and was diagnosed with enlarged lymph nodes in the neck, and the nodes were as large as jujubes with medium hardness and were relatively solid. After the patient took the carrimycin tablets (prepared in Embodiment 1) for 3 courses (30 days for 1 course, administered orally, 2 tablets per day), the attending physician diagnosed that lymph node enlargement was relieved, the lymph nodes became as small as soys, and the patient also felt relieved in terms that the hardness of the nodes decreased, and the patient's symptom was obviously improved.

Some patient had colon cancer and was diagnosed as a tumor or a mass that might be infiltrated with the omentum, and surrounding tissues. The tumor or the mass was hard and had an irregular shape. After the patient took the carrimycin tablets (prepared in Embodiment 1) for 1 course (30 days for 1 course, administered orally, 2 tablets per day), the attending physician diagnosed that the mass was reduced and the patient felt a significant improvement.

Some patient had leukemia with various degrees of anemia, bleeding, infection with fever, enlarged liver, spleen and lymph nodes, and bone pains. After the patient took the carrimycin tablets (prepared in Embodiment 1) for 3 courses (30 days for 1 course, administered orally, 2 tablets per day), the attending physician diagnosed that the symptoms decreased and the patients felt obviously improved.

Some patient had stomach adenocarcinoma. At first, the patient had stomachache, feeling that the stomach was bloated as if something was fermented there. And the stomach acid water occasionally rushed into the throat, making the throat hot and disgusting. The patient also felt hot and had cold sweats. Hospital examination showed stomach adenocarcinoma. After the patient took the carrimycin tablets (prepared in Embodiment 1) for 3 courses (30 days for 1 course, administered orally, 2 tablets per day), the attending physician diagnosed that the symptoms decreased and the patient felt a significant improvement.

Some patient had esophageal cancer. The esophageal barium meal X-ray film showed esophageal stricture, a rough wall tube, and mucosal destruction. And the patient also felt progressive difficulty in swallowing. After the patient took the carrimycin tablets (prepared in Embodiment 1) for 2 courses (30 days for 1 course, administered orally, 2 tablets per day), the attending physician diagnosed that the symptoms decreased and the patient felt a significant improvement.

Some patient was diagnosed with pancreatic cancer with limb weakness, loss of appetite, nausea, vomiting, and diarrhea. After the patient took the carrimycin tablets (prepared in Embodiment 1) for 2 courses (30 days for 1 course, administered orally, 2 tablets per day), the attending physician diagnosed that the symptoms decreased and the patient felt a significant improvement.

Some patient was diagnosed with prostate cancer. The gradually increasing prostate gland compressed the urinary tract of the patient and caused progressive dysuria, manifesting by fine urinary line, short range, slow urine flow, interruption of urinary flow, post-urine drip, incomplete urination, and laborious urination. In addition, there were frequent micturition, urgent urination, nocturia, and even urinary incontinence. Tumor compression of the rectum can cause difficulty in bowel or intestinal obstruction. After the patient took the carrimycin tablets (prepared in Embodiment 1) for 2 courses, the attending physician diagnosed that the symptoms decreased and the patient felt a significant improvement.

Some patient had lung cancer, liver cancer and metastasis to advanced bone cancer. The patient was hospitalized due to vomiting, cough, or bone pains. After the patient took 4 boxes of carrimycin tablets (prepared in Embodiment 1), the hospital examination found lung tumor calcification, and lung tumor disappeared.

Some patient had lung cancer with a lesion around the upper lobe of the right lung, and went to a doctor due to difficulty in breathing and a severe cough. CT examination: peripheral lesions of the right upper lobe, 4.3*4.6 round-like mass opacities; enhanced CT: mass size 4.0*4.4, other changes were not significant. The patient took carrimycin with the dose of 2 tablets of carrimycin (prepared in Embodiment 1) per day*14 days, then 1 tablet/day to date, with the auxiliary dose of calf thymosin 6 capsules/day. CT examination showed that the round-like mass opacities were significantly reduced, and the patient's mental state was good and there was no discomfort.

Some patient had cervical cancer that had transferred to other parts of the lungs, bones, and intestine. CT examination showed that the lungs had pleural effusion and multiple nodules. The patient had breathing difficulties and fever, and received chemotherapy and radiotherapy treatment. After the patient took the carrimycin tablets (prepared in Embodiment 1) for 2 courses, a new CT examination revealed that the pleural effusion disappeared and the nodules became smaller.

Test Example 4. Toxicology Test

1. Acute toxicity test
1.1 Test Purpose

It is the object of the test to determine the severity of toxicity, death and half lethal dose $LD_{50}$ of canine receiving one-time administration of carrimycin by perfusion, and to provide a reference for a long-term toxicity test.

1.2 Test Drug:
Name: Carrimycin
Potency: 927 U/mg

Preparation method: the appropriate amount of carrimycin was weighed, and was grinded into a powder. Then an appropriate amount of 0.5% carboxymethyl cellulose solution was added to the powder, the mixture was further stirred and mixed, and was prepared into 100 mg/ml for oral administration.

Solvent: 0.5% carboxymethyl cellulose solution
1.3 Animal: Canine
Source: Animal Feeding Farm, Fuwai Cardiovascular Hospital, Chinese Academy of Medical Sciences
Species: Hybrid
Certificate No.: Jing Dong Guan Quan Zi (96) No. 024
Weight: 15-20 kg
Gender: Male
Fasting time: 12 hours
Number of animals per group: 1-2
1.4 Experiment Method After preliminary pre-test, canines were orally administered with 2,000 mg/kg and 3,000 mg/kg of carrimycin, and no death or serious toxicity was observed. According to the new drug guidelines, the dose was increased by 50%, that is, increased to 4,500 mg/kg. The carrimycin was weighed according to the weight of canines and fully suspended with 0.5% CMC before it was orally administered to canines with a gastric tube (fasting overnight before the test). The toxicity and death were observed for one week after administration.

1.5 Acute Oral Toxicity in Canines
1.5.1 Toxic Reaction

In the pre-test, the canines were administered intragastrically with the doses of 2,000 mg/kg and 3,000 mg/kg of carrimycin, and they only had a brief vomiting reaction, spitting out the drug residue, gastric juice and food residue.

No other toxicity is observed except for the vomiting reaction. In the formal test, the two canines were orally administered with a dose of 4,500 mg/kg, respectively, and the toxic reaction is still gastrointestinal symptoms such as vomiting. No diarrhea or loose stools were observed, and no obvious other toxicity symptoms were observed after the vomiting reaction.

1.5.2 Half Lethal Dose

After two pre-test oral doses of 2,000 mg/kg and 3,000 mg/kg, only gastrointestinal symptoms such as vomiting were presented in canines. According to the guidelines for the approval of new drugs, the formal test dose is 4,500 mg/kg according to the 50% increment method. Both canines after intragastric administration show a vomiting reaction, and no other toxic reactions were observed. The $LD_{50}$ of canines receiving oral administration of carrimycin is >4,500 mg/kg.

TABLE 45

Acute toxicity of canines receiving oral administration of carrimycin ($LD_{50}$)

| Dose (mg/kg) | Logarithmic Dose | Number of Animals | Number of Dead Animals | Death Rate (%) | LD50 (mg/kg) |
|---|---|---|---|---|---|
| 2000 | 3.3 | 1 | 0 | 0 | >2000 |
| 3000 | 3.5 | 1 | 0 | 0 | >3000 |
| 4500 | 3.7 | 2 | 0 | 0 | >4500 |

2. Micronucleus Test of Carrimycin on Rodents 2.1 Test Purpose

It is the object to test the mutagenic potential of drugs on mammalian somatic cells, and provide a basis for clinical drug use.

2.2 Test Drug

Name: Carrimycin

Content: potency 927 U/mg

Preparation method: an appropriate amount of carrimycin fine powder was weighed according to the dose and was grinded in a mortar. An appropriate amount of 0.5% sodium carboxymethyl cellulose solution was added to prepare a suspension, and the suspension was stored in a refrigerator at 4° C. The negative control was an equal amount of 0.5% sodium carboxymethylcellulose solution. The positive control was prepared as follows: an appropriate amount of cyclophosphamide used for injection was weighed, and was dissolved in normal saline at the time of use to prepare 60 mg/kg of solution.

Solvent, excipient: normal saline, 0.5% sodium carboxymethyl cellulose solution

Control: positive control: 60 mg/kg cyclophosphamide solution negative control: 0.5% sodium carboxymethylcellulose 2.3 Animals Sexually mature male NIH mice are selected and provided by the China National Institute for the Control of Pharmaceutical and Biological Products.

2.4 Experiment Method 6 mice per group. The doses, number of administrations, and bone marrow sampling time are selected in the pre-test.

TABLE 46

Pre-test results of carrimycin on micronucleus test of mouse bone marrow polychromatic erythrocytes

| Sampling Time (Hours) | Dose (mg/kg) | Number of Animals | Number of Erythrocytes Tested | Number of Micronuclei |
|---|---|---|---|---|
| 12 | 2000 | 2 | 2008 | 3 |
| 18 | 2000 | 2 | 2000 | 2 |
| 24 | 2000 | 2 | 2003 | 4 |
| 48 | 2000 | 2 | 2006 | 3 |
| 72 | 2000 | 2 | 2009 | 3 |

The dose is reduced by ½ $LD_{50}$ as the standard, and the number of administrations is one time. According to the pre-test results, the bone marrow sampling time is to sample 24 hours after administration.

2.4.1 Dose

At least three dose groups, respectively: 2,000 mg/kg, 1,000 mg/kg, 500 mg/kg

Dose distance: 0.5

The number of administrations: one-time oral administration.

2.4.2 Administration Route

Oral (Intragastric) administration.

2.4.3 Bone marrow sampling time: 24 hours after administration.

2.4.4 Specimen production: animal sacrifice, smear, fixation, and staining.

2.4.5 Method:

The mice were sacrificed by cervical dislocation. Then the sternums were taken to remove the muscles thereon and the attachments were wiped with a gauze. Direct smear of bone marrow was used: the sternums were cut to expose the medullary cavity, and bone marrow was extruded and mixed well with a drop of calf serum on a slide beforehand as a push piece. After being dried, the slide was fixed in methanol for 10 minutes, and then after it was dried, it was then subjected to Giemsa staining. Each mouse was microscopically examined for about 1,000 polychromatic erythrocytes with intact contours of erythrocytes, and the frequency of occurrence of micronuclei and the ratio of polychromatic erythrocytes to erythrocytes were counted.

2.5 The results of carrimycin on the micronucleus test of mouse polychromatic erythrocytes are shown in the Table below.

2.5.1 The Frequency of Occurrence of Micronuclei of Polychromatic Erythrocytes

TABLE 47

The frequency of occurrence of micronuclei of polychromatic erythrocytes

| Experiment Group | Dose (mg/kg) | Number of Animals | Number of Polychromatic Erythrocytes (N) | Number of Micronuclei | Number of Cells Tested |
|---|---|---|---|---|---|
| Negative Control | | 6 | 4261 | 16 | 6090 |
| Carrimycin | 500 | 6 | 4494 | 18 | 6000 |
| | 1000 | 6 | 4543 | 16 | 6055 |
| | 2000 | 6 | 4364 | 21 | 6000 |
| Positive Control | 60 | 6 | 3502 | 266 | 6000 |

2.5.2 Ratio of Polychromatic Erythrocytes to Normal Erythrocytes

TABLE 48

Ratio of polychromatic erythrocytes to normal erythrocytes

| Experiment Group | Dose (mg/kg) | Number of Animals | Number of Polychromatic Erythrocytes (N) | Normal Erythrocytes (P) | P/N | Number of Cells Tested |
|---|---|---|---|---|---|---|
| Negative Control | | 6 | 4261 | 1829 | 0.43 | 6090 |
| Carrimycin | 500 | 6 | 4494 | 1506 | 0.34 | 6000 |
| | 1000 | 6 | 4543 | 1512 | 0.33 | 6055 |
| | 2000 | 6 | 4364 | 1636 | 0.38 | 6000 |
| Positive Control | 60 | 6 | 3502 | 2498 | 0.71 | 6000 |

2.5.3 Effect of Carrimycin on Micronuclei of Mouse Bone Marrow Polychromatic Erythrocytes

TABLE 49

Effect of carrimycin on micronuclei of mouse bone marrow polychromatic erythrocytes

| Experiment Group | Dose (mg/kg) | Number of Animals | Polychromatic Erythrocytes (N) | P/N Ratio | Number of Micronuclei | mean ± S |
|---|---|---|---|---|---|---|
| Negative Control | | 6 | 4261 | 0.43 | 16 | 2.63 ± 1.21 |
| Carrimycin | 500 | 6 | 4494 | 0.34 | 18 | 3.00 ± 0.89 |
| | 1000 | 6 | 4543 | 0.33 | 16 | 2.64 ± 1.37 |
| | 2000 | 6 | 4354 | 0.38 | 21 | 3.50 ± 1.05 |
| Positive Control | 60 | 6 | 3502 | 0.71 | 266 | 44.33 ± 11.08** |

*P/N normal erythrocytes/polychromatic erythrocytes
**P < 0.01

Heddle et al report that the spontaneous rate of micronuclei of 16 mouse bone marrow polychromatic erythrocytes is 3.1‰. In the study of the present disclosure, the average value of the negative control group is 2.63‰. And compared with the negative control group, the three dose groups of carrimycin do not have significant increase in the micronucleus rate of polychromatic erythrocytes (P>0.05). The ratio of polychromatic erythrocytes to normal erythrocytes does not significantly reduce, and fluctuations are in the normal range. Compared with the negative control group, the cyclophosphamide positive control group has a very significant increase in micronuclei of polychromatic erythrocytes (P<0.01), and the micronucleus rate is 16.85 times that of the negative control group.

2.6 Conclusion

The above results indicate that carrimycin is not a chromosomal cleavage agent. And when the carrimycin is administered in the dose used, the carrimycin does not affect the normal mitosis of the cells and has no inhibitory effect on the bone marrow.

The above are only preferred embodiments of the present disclosure, and are not intended to limit the present disclosure in any form. Although the present disclosure has been disclosed in the above preferred embodiments, they are not intended to limit the present disclosure. Any technician who is familiar with the present disclosure can make a slight change or modification into the equivalent embodiments of equivalent changes by using the technical content of the above-mentioned hints without departing from the scope of the technical solution of the present disclosure. But as long as the technical content is not deviated from the technical solution of the present disclosure, any simple modifications, equivalent changes and modifications made to the above embodiments according to the technical substance of the present disclosure are still within the scope of the present disclosure.

The invention claimed is:

1. A method for treating tumor, comprising administering a medicament comprising carrimycin or a pharmaceutically acceptable salt thereof to a subject,
    wherein the tumor includes breast cancer, liver cancer, lung cancer, renal cancer, brain tumor, cervical cancer, prostate cancer, pancreatic cancer, esophageal cancer, gastric cancer, colon cancer, lymphoma or leukemia.

2. The method according to claim 1, wherein the medicament further comprises a pharmaceutically acceptable adjuvants.

3. The method according to claim 1, wherein the medicament further comprises an anti-tumor drug and a pharmaceutically acceptable adjuvants.

4. The method according to claim 1, wherein the medicament is a combination of a first agent and a second agent, the first agent contains carrimycin or the pharmaceutically acceptable salt thereof, and the second agent contains an anti-tumor drug.

5. The method according to claim 3, wherein the anti-tumor drug is one or more selected from the group consisting of a chemotherapy drug, a radiotherapy drug, a targeted therapy drug, and an immunotherapeutic drug.

6. The method according to claim 2, wherein a dose of the medicament is in a range from 5 to 1,500 mg.

7. The method according to claim 4, wherein a dose of the first agent is in a range from 5 to 1,500 mg.

8. The method according to claim 1, wherein the brain tumor is glioma or meningioma, and the gastric cancer is gastric adenocarcinoma.

9. The method according to claim 4, wherein the anti-tumor drug is one or more than one drug selected from the group containing consisting of a chemotherapy drug, a radiotherapy drug, a targeted therapy drug, and an immunotherapeutic drug.

10. The method according to claim 3, wherein a dose of the medicament is in a range from 5 to 1,500 mg.

11. The method according to claim 6, wherein the dose of the medicament is in a range from 50 to 1,000 mg.

12. The method according to claim 11, wherein the dose of the medicament is in a range from 100 to 400 mg.

13. The method according to claim 7, wherein the dose of the first agent is in a range from 50 to 1,000 mg.

14. The method according to claim 13, wherein the dose of the first agent is in a range from 100 to 400 mg.

\* \* \* \* \*